US009625361B1

(12) United States Patent
Vail, III

(10) Patent No.: US 9,625,361 B1
(45) Date of Patent: *Apr. 18, 2017

(54) METHODS AND APPARATUS TO PREVENT FAILURES OF FIBER-REINFORCED COMPOSITE MATERIALS UNDER COMPRESSIVE STRESSES CAUSED BY FLUIDS AND GASES INVADING MICROFRACTURES IN THE MATERIALS

(71) Applicant: Smart Drilling and Completion, Inc., Bothell, WA (US)

(72) Inventor: William Banning Vail, III, Bothell, WA (US)

(73) Assignee: Smart Drilling and Completion, Inc., Bothell, WA (US)

(*) Notice: Subject to any disclaimer, the term of this patent is extended or adjusted under 35 U.S.C. 154(b) by 682 days.

This patent is subject to a terminal disclaimer.

(21) Appl. No.: 13/966,172

(22) Filed: Aug. 13, 2013

Related U.S. Application Data

(63) Continuation-in-part of application No. 12/804,039, filed on Jul. 12, 2010, now Pat. No. 8,515,677, which
(Continued)

(51) Int. Cl.
*G01N 15/08* (2006.01)
*G01L 1/00* (2006.01)
(Continued)

(52) U.S. Cl.
CPC .......... *G01N 3/08* (2013.01); *B64C 1/26* (2013.01); *B64C 2001/0072* (2013.01); *Y02T 50/433* (2013.01); *Y10T 428/1369* (2015.01)

(58) Field of Classification Search
CPC ..... B64C 1/26; B64C 2001/0072; E21B 4/04; Y02T 50/433; G02F 1/15; G02F 1/163; Y10T 428/1369
(Continued)

(56) References Cited

U.S. PATENT DOCUMENTS

| 972,308 A | 10/1910 | Williamson |
| 3,670,566 A | 6/1972 | Basham et al. |

(Continued)

FOREIGN PATENT DOCUMENTS

| EP | 0553908 | 8/1993 |
| EP | 0571045 | 11/1993 |

(Continued)

OTHER PUBLICATIONS

U.S. Appl. No. 14/167,766, filed Jan. 29, 2014, Vail et al.
(Continued)

*Primary Examiner* — John H Le
(74) *Attorney, Agent, or Firm* — Sheridan Ross P.C.

(57) ABSTRACT

Methods and apparatus are described to use real-time measurement systems to detect the onset of compression induced micro-fracturing of fiber-reinforced composite materials. Measurements are described to detect the onset of compression induced micro-fracturing of fiber-reinforced composite materials to prevent catastrophic failures of aircraft components containing such materials. Methods and apparatus are described to prevent fluids and gases from invading any compression induced microfractures by coating surfaces of fiber-reinforced materials to reduce the probability of failure of such fiber-reinforced materials.

6 Claims, 6 Drawing Sheets

Related U.S. Application Data is a continuation-in-part of application No. 12/583,240, filed on Aug. 17, 2009, now Pat. No. 8,353,348, which is a continuation-in-part of application No. 12/005,105, filed on Dec. 22, 2007, now abandoned, which is a continuation-in-part of application No. 10/800,443, filed on Mar. 14, 2004, now Pat. No. 7,311,151, which is a continuation-in-part of application No. 10/729,509, filed on Dec. 4, 2003, now Pat. No. 7,032,658, which is a continuation-in-part of application No. 10/223,025, filed on Aug. 15, 2002, now Pat. No. 6,857,486.

(60) Provisional application No. 61/850,774, filed on Feb. 22, 2013, provisional application No. 61/850,095, filed on Feb. 9, 2013, provisional application No. 61/849,968, filed on Feb. 6, 2013, provisional application No. 61/849,585, filed on Jan. 29, 2013, provisional application No. 61/270,709, filed on Jul. 10, 2009, provisional application No. 61/396,518, filed on May 29, 2010, provisional application No. 60/455,657, filed on Mar. 18, 2003, provisional application No. 60/504,359, filed on Sep. 20, 2003, provisional application No. 60/532,023, filed on Dec. 22, 2003, provisional application No. 60/535,395, filed on Jan. 10, 2004, provisional application No. 60/523,894, filed on Nov. 20, 2003, provisional application No. 60/432,045, filed on Dec. 8, 2002, provisional application No. 60/448,191, filed on Feb. 18, 2003, provisional application No. 60/523,894, filed on Nov. 20, 2003, provisional application No. 60/504,359, filed on Sep. 20, 2003, provisional application No. 60/455,657, filed on Mar. 18, 2003.

(51) Int. Cl.
  *G01N 3/08* (2006.01)
  *B64C 1/26* (2006.01)
  *B64C 1/00* (2006.01)

(58) Field of Classification Search
  USPC ...... 702/9, 12, 34, 42, 43, 53, 59, 144, 181; 73/777; 138/125; 166/61, 302, 367; 264/108
  See application file for complete search history.

(56) References Cited

U.S. PATENT DOCUMENTS

| | | |
|---|---|---|
| 3,755,713 A | 8/1973 | Paszkowski |
| 3,814,275 A | 6/1974 | Lemons |
| 3,837,412 A | 9/1974 | Driver |
| 3,878,312 A | 4/1975 | Bergh et al. |
| 3,881,972 A | 5/1975 | Long |
| 3,910,105 A | 10/1975 | Hoffstedt |
| 3,936,277 A | 2/1976 | Jakway et al. |
| 3,939,024 A | 2/1976 | Hoggatt |
| 3,951,718 A | 4/1976 | Gonzalez |
| 3,975,617 A | 8/1976 | Othmer |
| 3,978,256 A | 8/1976 | James |
| 4,016,943 A | 4/1977 | Cullen et al. |
| 4,031,969 A | 6/1977 | Cullen et al. |
| 4,038,118 A | 7/1977 | James |
| 4,051,908 A | 10/1977 | Driver |
| 4,057,116 A | 11/1977 | Striegler |
| 4,075,862 A | 2/1978 | Ames |
| 4,085,808 A | 4/1978 | Kling |
| 4,086,378 A | 4/1978 | Kam et al. |
| 4,095,865 A | 6/1978 | Denison et al. |
| 4,100,322 A | 7/1978 | Seibold et al. |
| 4,136,846 A | 1/1979 | Brault |
| 4,155,970 A | 5/1979 | Cassell |
| 4,175,620 A | 11/1979 | Nolan et al. |
| 4,198,018 A | 4/1980 | Brault |
| 4,215,161 A | 7/1980 | Seibold et al. |
| 4,216,047 A | 8/1980 | Hilliard et al. |
| 4,223,053 A | 9/1980 | Brogan |
| 4,247,255 A | 1/1981 | De Rosa |
| 4,256,146 A | 3/1981 | Genini et al. |
| 4,278,485 A | 7/1981 | Hamm et al. |
| 4,301,707 A | 11/1981 | Schimmel et al. |
| 4,318,954 A | 3/1982 | Jensen |
| 4,331,723 A | 5/1982 | Hamm |
| 4,336,415 A | 6/1982 | Walling |
| 4,367,980 A | 1/1983 | Ames et al. |
| 4,370,390 A | 1/1983 | Burk |
| 4,395,450 A | 7/1983 | Whitener |
| 4,460,531 A | 7/1984 | Harris et al. |
| 4,463,814 A | 8/1984 | Horstmeyer et al. |
| 4,469,730 A | 9/1984 | Burhans |
| 4,475,976 A | 10/1984 | Mittelstadt et al. |
| 4,538,682 A | 9/1985 | McManus et al. |
| 4,544,041 A | 10/1985 | Rinaldi |
| 4,556,439 A | 12/1985 | Bannink, Jr. |
| 4,556,591 A | 12/1985 | Bannink, Jr. |
| 4,556,592 A | 12/1985 | Bannink, Jr. |
| 4,557,538 A | 12/1985 | Chevalier |
| 4,565,595 A | 1/1986 | Whitener |
| 4,567,076 A | 1/1986 | Therrien |
| 4,571,355 A | 2/1986 | Elrod |
| 4,579,699 A | 4/1986 | Verzemnieks |
| 4,606,961 A | 8/1986 | Munsen et al. |
| 4,615,935 A | 10/1986 | Bendig et al. |
| 4,622,091 A | 11/1986 | Letterman |
| 4,625,095 A | 11/1986 | Das |
| 4,636,422 A | 1/1987 | Harris et al. |
| 4,655,417 A | 4/1987 | Herndon |
| 4,676,310 A | 6/1987 | Scherbatskoy et al. |
| 4,683,368 A | 7/1987 | Das |
| 4,696,711 A | 9/1987 | Greszczuk |
| 4,715,923 A | 12/1987 | Knoll |
| 4,720,255 A | 1/1988 | Mittelstadt |
| 4,726,924 A | 2/1988 | Mittelstadt |
| 4,741,943 A | 5/1988 | Hunt |
| 4,749,155 A | 6/1988 | Hammer et al. |
| 4,752,537 A | 6/1988 | Das |
| 4,755,904 A | 7/1988 | Brick |
| 4,765,602 A | 8/1988 | Roeseler |
| 4,765,942 A | 8/1988 | Christensen et al. |
| 4,767,656 A | 8/1988 | Chee et al. |
| 4,786,343 A | 11/1988 | Hertzberg |
| 4,789,416 A | 12/1988 | Ford |
| 4,793,409 A | 12/1988 | Bridges et al. |
| 4,797,155 A | 1/1989 | Das |
| 4,806,115 A | 2/1989 | Chevalier et al. |
| 4,842,081 A | 6/1989 | Parant |
| 4,847,333 A | 7/1989 | Lubowitz et al. |
| 4,851,501 A | 7/1989 | Lubowitz et al. |
| 4,859,267 A | 8/1989 | Knoll |
| 4,868,270 A | 9/1989 | Lubowitz et al. |
| 4,874,925 A | 10/1989 | Dickenson |
| 4,876,328 A | 10/1989 | Lubowitz et al. |
| 4,877,375 A | 10/1989 | Desjardins |
| 4,883,971 A | 11/1989 | Jensen |
| 4,884,772 A | 12/1989 | Kraft |
| 4,895,426 A | 1/1990 | Pinson |
| 4,898,754 A | 2/1990 | Christensen et al. |
| 4,900,383 A | 2/1990 | Dursch et al. |
| 4,917,747 A | 4/1990 | Chin et al. |
| 4,965,336 A | 10/1990 | Lubowitz et al. |
| 4,966,802 A | 10/1990 | Hertzberg |
| 4,988,389 A | 1/1991 | Adamache et al. |
| 4,988,398 A | 1/1991 | Pereman et al. |
| 5,011,905 A | 4/1991 | Lubowitz et al. |
| 5,013,507 A | 5/1991 | Julien et al. |
| 5,023,987 A | 6/1991 | Wuepper et al. |
| 5,031,995 A | 7/1991 | Pinson |
| 5,042,967 A | 8/1991 | Desjardins |
| 5,051,226 A | 9/1991 | Brustad et al. |
| 5,060,737 A | 10/1991 | Mohn |

(56) References Cited

U.S. PATENT DOCUMENTS

| | | |
|---|---|---|
| 5,066,541 A | 11/1991 | Lubowitz et al. |
| 5,069,318 A | 12/1991 | Kulesha et al. |
| 5,070,533 A | 12/1991 | Bridges et al. |
| 5,071,319 A | 12/1991 | McCafferty |
| 5,071,941 A | 12/1991 | Lubowitz et al. |
| 5,077,106 A | 12/1991 | Dursch et al. |
| 5,082,905 A | 1/1992 | Lubowitz et al. |
| 5,085,921 A | 2/1992 | Jayarajan |
| 5,099,918 A | 3/1992 | Bridges et al. |
| 5,104,967 A | 4/1992 | Sheppard et al. |
| 5,112,939 A | 5/1992 | Lubowitz et al. |
| 5,115,087 A | 5/1992 | Sheppard et al. |
| 5,120,819 A | 6/1992 | Lubowitz et al. |
| 5,122,176 A | 6/1992 | Goettler |
| 5,126,410 A | 6/1992 | Lubowitz et al. |
| 5,129,452 A | 7/1992 | Wilson |
| 5,148,875 A | 9/1992 | Karlsson et al. |
| 5,159,055 A | 10/1992 | Sheppard et al. |
| 5,172,765 A | 12/1992 | Sas-Jaworsky et al. |
| 5,175,233 A | 12/1992 | Lubowitz et al. |
| 5,175,234 A | 12/1992 | Lubowitz et al. |
| 5,176,180 A | 1/1993 | Williams et al. |
| 5,197,553 A | 3/1993 | Leturno |
| 5,198,282 A | 3/1993 | Baker et al. |
| 5,198,526 A | 3/1993 | Lubowitz et al. |
| 5,216,117 A | 6/1993 | Sheppard et al. |
| 5,227,216 A | 7/1993 | Pettit |
| 5,235,259 A | 8/1993 | Dhindsa et al. |
| 5,239,822 A | 8/1993 | Buchacher |
| 5,248,242 A | 9/1993 | Lallo et al. |
| 5,268,519 A | 12/1993 | Sheppard et al. |
| 5,271,472 A | 12/1993 | Leturno |
| 5,284,996 A | 2/1994 | Vickers |
| 5,285,008 A | 2/1994 | Sas-Jaworsky et al. |
| 5,285,846 A | 2/1994 | Mohn |
| 5,286,811 A | 2/1994 | Lubowitz et al. |
| 5,289,561 A | 2/1994 | Costa Filho |
| 5,305,830 A | 4/1994 | Wittrisch |
| 5,332,048 A | 7/1994 | Underwood et al. |
| 5,344,894 A | 9/1994 | Lubowitz et al. |
| 5,345,397 A | 9/1994 | Handel et al. |
| 5,353,872 A | 10/1994 | Wittrisch |
| 5,368,807 A | 11/1994 | Lindsay |
| 5,376,598 A | 12/1994 | Preedy et al. |
| 5,378,109 A | 1/1995 | Lallo et al. |
| 5,392,715 A | 2/1995 | Pelrine |
| 5,403,666 A | 4/1995 | Lubowitz et al. |
| 5,404,953 A | 4/1995 | Sangesland |
| 5,410,133 A | 4/1995 | Matsen et al. |
| 5,425,973 A | 6/1995 | Frangipane et al. |
| 5,428,706 A | 6/1995 | Lequeux |
| 5,446,120 A | 8/1995 | Lubowitz et al. |
| 5,447,680 A | 9/1995 | Bowden |
| 5,467,832 A | 11/1995 | Orban et al. |
| 5,472,057 A | 12/1995 | Winfree |
| 5,484,277 A | 1/1996 | Lindsay |
| 5,497,840 A | 3/1996 | Hudson |
| 5,506,060 A | 4/1996 | Lubowitz et al. |
| 5,521,014 A | 5/1996 | Lubowitz et al. |
| 5,530,089 A | 6/1996 | Sheppard et al. |
| 5,530,228 A | 6/1996 | Burnett et al. |
| 5,551,521 A | 9/1996 | Vail, III |
| 5,553,678 A | 9/1996 | Barr et al. |
| 5,556,565 A | 9/1996 | Kirkwood et al. |
| 5,569,343 A | 10/1996 | Garrigus |
| 5,582,259 A | 12/1996 | Barr |
| 5,591,369 A | 1/1997 | Matsen et al. |
| 5,594,089 A | 1/1997 | Lubowtiz et al. |
| 5,613,567 A | 3/1997 | Hudson |
| 5,645,925 A | 7/1997 | Sheppard et al. |
| 5,654,396 A | 8/1997 | Lubowitz et al. |
| 5,667,011 A | 9/1997 | Gill et al. |
| 5,686,038 A | 11/1997 | Christensen et al. |
| 5,688,426 A | 11/1997 | Kirkwood et al. |
| 5,693,741 A | 12/1997 | Sheppard et al. |
| 5,695,008 A | 12/1997 | Bertet et al. |
| 5,705,795 A | 1/1998 | Anderson et al. |
| 5,705,796 A | 1/1998 | Hansen et al. |
| 5,707,576 A | 1/1998 | Asher |
| 5,707,723 A | 1/1998 | Harrison et al. |
| 5,710,412 A | 1/1998 | Hansen |
| 5,717,191 A | 2/1998 | Christensen et al. |
| 5,723,849 A | 3/1998 | Matsen et al. |
| 5,736,222 A | 4/1998 | Childress |
| 5,753,570 A | 5/1998 | Garrigus |
| 5,756,973 A | 5/1998 | Kirkwood et al. |
| 5,759,699 A | 6/1998 | French |
| 5,760,379 A | 6/1998 | Matsen et al. |
| 5,769,160 A | 6/1998 | Owens |
| 5,780,583 A | 7/1998 | Lubowitz et al. |
| 5,782,301 A | 7/1998 | Neuroth et al. |
| 5,793,024 A | 8/1998 | Matsen et al. |
| 5,797,239 A | 8/1998 | Zaccone et al. |
| 5,807,593 A | 9/1998 | Thompson |
| 5,817,738 A | 10/1998 | Lubowitz et al. |
| 5,820,344 A | 10/1998 | Hamilton et al. |
| 5,828,003 A | 10/1998 | Thomeer et al. |
| 5,829,716 A | 11/1998 | Kirkwood et al. |
| 5,833,795 A | 11/1998 | Smith et al. |
| 5,837,318 A | 11/1998 | French |
| 5,842,149 A | 11/1998 | Harrell et al. |
| 5,845,722 A | 12/1998 | Makohl et al. |
| 5,847,375 A | 12/1998 | Matsen et al. |
| 5,848,767 A | 12/1998 | Cappa et al. |
| 5,849,234 A | 12/1998 | Harrison et al. |
| 5,862,975 A | 1/1999 | Childress |
| 5,863,635 A | 1/1999 | Childress |
| 5,866,272 A | 2/1999 | Westre et al. |
| 5,869,165 A | 2/1999 | Rorabaugh et al. |
| 5,876,540 A | 3/1999 | Pannell |
| 5,876,652 A | 3/1999 | Rorabaugh et al. |
| 5,882,462 A | 3/1999 | Donecker et al. |
| 5,882,756 A | 3/1999 | Alston et al. |
| 5,890,537 A | 4/1999 | Lavaure et al. |
| 5,894,897 A | 4/1999 | Vail, III |
| 5,895,699 A | 4/1999 | Corbett et al. |
| 5,908,049 A | 6/1999 | Williams et al. |
| 5,910,348 A | 6/1999 | Hart-Smith et al. |
| 5,913,337 A | 6/1999 | Williams et al. |
| 5,916,469 A | 6/1999 | Scoles et al. |
| 5,919,543 A | 7/1999 | McCarville et al. |
| 5,921,285 A | 7/1999 | Quigley et al. |
| 5,935,475 A | 8/1999 | Scoles et al. |
| 5,935,680 A | 8/1999 | Childress |
| 5,935,698 A | 8/1999 | Pannell |
| 5,944,060 A | 8/1999 | MacKay |
| 5,955,387 A | 9/1999 | Garrigus |
| 5,958,550 A | 9/1999 | Childress |
| 5,958,578 A | 9/1999 | Blohowiak et al. |
| 5,968,639 A | 10/1999 | Childress |
| 5,969,079 A | 10/1999 | Lubowitz et al. |
| 5,972,524 A | 10/1999 | Childress |
| 5,975,237 A | 11/1999 | Welch et al. |
| 5,980,665 A | 11/1999 | Childress |
| 6,004,639 A | 12/1999 | Quigley et al. |
| 6,009,825 A | 1/2000 | Fulton et al. |
| RE36,556 E | 2/2000 | Smith et al. |
| 6,024,555 A | 2/2000 | Goodridge et al. |
| 6,027,798 A | 2/2000 | Childress |
| 6,029,269 A | 2/2000 | El-Soudani |
| 6,031,371 A | 2/2000 | Smart |
| 6,036,802 A | 3/2000 | Banks et al. |
| 6,041,860 A | 3/2000 | Nazzal et al. |
| 6,049,657 A | 4/2000 | Sumner |
| 6,051,089 A | 4/2000 | Palmer et al. |
| 6,051,302 A | 4/2000 | Moore |
| 6,064,031 A | 5/2000 | Talwar |
| 6,074,716 A | 6/2000 | Tsotsis |
| 6,086,975 A | 7/2000 | Brick et al. |
| 6,092,610 A | 7/2000 | Kosmala et al. |
| 6,112,808 A | 9/2000 | Isted |
| 6,112,809 A | 9/2000 | Angle |
| 6,114,050 A | 9/2000 | Westre et al. |
| 6,122,884 A | 9/2000 | Talwar |

(56) References Cited

U.S. PATENT DOCUMENTS

| | | |
|---|---|---|
| 6,129,311 A | 10/2000 | Welch et al. |
| 6,136,237 A | 10/2000 | Straub et al. |
| 6,148,664 A | 11/2000 | Baird |
| 6,148,866 A | 11/2000 | Quigley et al. |
| 6,158,531 A | 12/2000 | Vail, III |
| 6,180,206 B1 | 1/2001 | Kain, Jr. |
| 6,183,125 B1 | 2/2001 | Hara et al. |
| 6,189,621 B1 | 2/2001 | Vail, III |
| 6,196,336 B1 | 3/2001 | Fincher et al. |
| 6,216,533 B1 | 4/2001 | Woloson et al. |
| 6,257,162 B1 | 7/2001 | Watt et al. |
| 6,257,332 B1 | 7/2001 | Vidrine et al. |
| 6,263,987 B1 | 7/2001 | Vail, III |
| 6,264,401 B1 | 7/2001 | Langner et al. |
| 6,270,603 B1 | 8/2001 | Westerman et al. |
| 6,273,189 B1 | 8/2001 | Gissler |
| 6,277,463 B1 | 8/2001 | Hamilton et al. |
| 6,278,095 B1 | 8/2001 | Bass et al. |
| 6,284,089 B1 | 9/2001 | Anderson et al. |
| 6,286,558 B1 | 9/2001 | Quigley et al. |
| 6,296,066 B1 | 10/2001 | Terry et al. |
| 6,318,467 B1 | 11/2001 | Liu et al. |
| 6,325,148 B1 | 12/2001 | Trahan et al. |
| 6,343,649 B1 | 2/2002 | Beck et al. |
| 6,354,373 B1 | 3/2002 | Vercamer et al. |
| 6,357,485 B2 | 3/2002 | Quigley et al. |
| 6,359,569 B2 | 3/2002 | Beck et al. |
| 6,361,299 B1 | 3/2002 | Quigley et al. |
| 6,371,203 B2 | 4/2002 | Frank et al. |
| 6,371,693 B1 | 4/2002 | Kopp et al. |
| 6,374,924 B1 | 4/2002 | Hanton et al. |
| 6,379,762 B1 | 4/2002 | Omichinski |
| 6,397,946 B1 | 6/2002 | Vail, III |
| 6,408,943 B1 | 6/2002 | Schultz et al. |
| 6,412,562 B1 | 7/2002 | Shaw |
| 6,419,014 B1 | 7/2002 | Meek et al. |
| 6,419,033 B1 | 7/2002 | Hahn et al. |
| 6,431,282 B1 | 8/2002 | Bosma et al. |
| 6,432,507 B1 | 8/2002 | Brick et al. |
| 6,436,507 B1 | 8/2002 | Pannell |
| 6,440,521 B1 | 8/2002 | Moore |
| 6,484,818 B2 | 11/2002 | Alft et al. |
| 6,485,228 B1 | 11/2002 | Komatsu |
| 6,497,280 B2 | 12/2002 | Beck et al. |
| 6,506,499 B1 | 1/2003 | Blohowiak et al. |
| 6,509,557 B1 | 1/2003 | Bass |
| 6,536,522 B2 | 3/2003 | Birckhead et al. |
| 6,538,576 B1 | 3/2003 | Schultz et al. |
| 6,543,538 B2 | 4/2003 | Tolman et al. |
| 6,544,366 B2 | 4/2003 | Hamilton et al. |
| 6,554,064 B1 | 4/2003 | Restarick et al. |
| 6,562,436 B2 | 5/2003 | George et al. |
| 6,569,954 B1 | 5/2003 | Sheppard et al. |
| 6,578,636 B2 | 6/2003 | Mazorow et al. |
| 6,592,799 B1 | 7/2003 | Christensen et al. |
| 6,595,751 B1 | 7/2003 | Straub et al. |
| 6,604,550 B2 | 8/2003 | Quigley et al. |
| 6,613,169 B2 | 9/2003 | Georgeson et al. |
| 6,615,845 B1 | 9/2003 | Abraskin et al. |
| 6,615,848 B2 | 9/2003 | Coats |
| 6,663,453 B2 | 12/2003 | Quigley et al. |
| 6,686,745 B2 | 2/2004 | Bass |
| 6,689,448 B2 | 2/2004 | George et al. |
| 6,695,052 B2 | 2/2004 | Branstetter et al. |
| 6,706,348 B2 | 3/2004 | Quigley et al. |
| 6,707,012 B2 | 3/2004 | Stone, Jr. |
| 6,709,538 B2 | 3/2004 | George et al. |
| 6,714,018 B2 | 3/2004 | Bass |
| 6,719,870 B2 | 4/2004 | Ludin et al. |
| 6,739,803 B2 | 5/2004 | Bass et al. |
| 6,758,386 B2 | 7/2004 | Marshall et al. |
| 6,761,783 B2 | 7/2004 | Keller et al. |
| 6,767,606 B2 | 7/2004 | Jackson et al. |
| 6,772,840 B2 | 8/2004 | Headworth |
| 6,797,376 B2 | 9/2004 | Anderson et al. |
| 6,814,146 B2 | 11/2004 | Bass et al. |
| 6,827,896 B2 | 12/2004 | Christensen et al. |
| 6,857,452 B2 | 2/2005 | Quigley et al. |
| 6,857,486 B2 | 2/2005 | Chitwood et al. |
| 6,858,117 B2 | 2/2005 | Berton et al. |
| 6,861,017 B1 | 3/2005 | McCarville et al. |
| 6,868,906 B1 | 3/2005 | Vail et al. |
| 6,902,199 B2 | 6/2005 | Colyer et al. |
| 6,918,839 B2 | 7/2005 | Holemans et al. |
| 7,032,658 B2 | 4/2006 | Chitwood et al. |
| 7,182,291 B2 | 2/2007 | Westre et al. |
| 7,281,688 B1 | 10/2007 | Cox et al. |
| 7,303,700 B2 | 12/2007 | Miller et al. |
| 7,311,151 B2 | 12/2007 | Chitwood et al. |
| 7,325,606 B1 | 2/2008 | Vail et al. |
| 7,334,782 B2 | 2/2008 | Woods et al. |
| 7,357,014 B2 | 4/2008 | Vaccaro et al. |
| 7,371,451 B2 | 5/2008 | Messinger |
| 7,387,277 B2 | 6/2008 | Kordel et al. |
| 7,398,586 B2 | 7/2008 | Prichard et al. |
| 7,431,981 B2 | 10/2008 | Schneider |
| 7,527,759 B2 | 5/2009 | Lee et al. |
| 7,531,058 B2 | 5/2009 | Grose et al. |
| 7,561,402 B2 | 7/2009 | Heeter |
| 7,599,164 B2 | 10/2009 | Heeter et al. |
| 7,605,593 B2 | 10/2009 | Brady |
| 7,622,066 B2 | 11/2009 | Brustad et al. |
| 7,655,168 B2 | 2/2010 | Jones et al. |
| 7,716,797 B2 | 5/2010 | Kismarton et al. |
| 7,721,495 B2 | 5/2010 | Kismarton |
| 7,730,784 B2 | 6/2010 | Georgeson et al. |
| 7,755,351 B2 | 7/2010 | Brady |
| 7,766,281 B2 | 8/2010 | Lorkowski et al. |
| 7,770,457 B2 | 8/2010 | Engelbart et al. |
| 7,790,277 B2 | 9/2010 | Wilenski et al. |
| 7,807,005 B2 | 10/2010 | Rubin et al. |
| 7,807,249 B2 | 10/2010 | Kismarton |
| 7,825,211 B2 | 11/2010 | Lubowitz et al. |
| 7,836,950 B2 | 11/2010 | Vail |
| 7,837,147 B2 | 11/2010 | Liguore et al. |
| 7,837,148 B2 | 11/2010 | Kismarton et al. |
| 7,841,421 B2 | 11/2010 | Kulesha |
| 7,861,411 B2 | 1/2011 | Lunin |
| 7,874,518 B2 | 1/2011 | Pham et al. |
| 7,895,810 B2 | 3/2011 | Benthien |
| 7,896,287 B2 | 3/2011 | Lunin |
| 7,896,294 B2 | 3/2011 | Dittrich |
| 7,926,252 B2 | 4/2011 | Dietrich et al. |
| 7,938,996 B2 | 5/2011 | Baughman et al. |
| 7,954,762 B2 | 6/2011 | Boren et al. |
| 7,956,327 B2 | 6/2011 | Shelley et al. |
| 7,963,125 B2 | 6/2011 | Wilenski et al. |
| 7,963,126 B2 | 6/2011 | Wilenski et al. |
| 7,968,170 B2 | 6/2011 | Albers et al. |
| 8,006,722 B2 | 8/2011 | Hesse et al. |
| 8,042,768 B2 | 10/2011 | Liguore et al. |
| 8,043,554 B2 | 10/2011 | Yip et al. |
| 8,044,354 B2 | 10/2011 | Werner et al. |
| 8,052,826 B2 | 11/2011 | Burpo et al. |
| 8,082,667 B2 | 12/2011 | Kulesha |
| 8,084,114 B2 | 12/2011 | Grose et al. |
| 8,097,106 B2 | 1/2012 | Hand et al. |
| 8,100,020 B2 | 1/2012 | Kinlen et al. |
| 8,132,430 B2 | 3/2012 | Wilenski et al. |
| 8,141,393 B2 | 3/2012 | Wilenski et al. |
| 8,142,181 B2 | 3/2012 | Willden et al. |
| 8,157,212 B2 | 4/2012 | Biornstad et al. |
| 8,157,469 B2 | 4/2012 | Kennedy |
| 8,158,210 B2 | 4/2012 | Kramp |
| 8,161,619 B2 | 4/2012 | Wanthal |
| 8,163,368 B2 | 4/2012 | Kismarton |
| 8,185,327 B2 | 5/2012 | Fogarty et al. |
| 8,205,833 B2 | 6/2012 | Kismarton et al. |
| 8,215,885 B2 | 7/2012 | Meisner et al. |
| 8,218,142 B2 | 7/2012 | Wilcken |
| 8,226,336 B2 | 7/2012 | Brady |
| 8,228,248 B1 | 7/2012 | Kahle et al. |
| 8,286,919 B2 | 10/2012 | Gerken et al. |
| 8,292,227 B2 | 10/2012 | Stuhr et al. |

(56) References Cited

U.S. PATENT DOCUMENTS

| | | | |
|---|---|---|---|
| 8,297,555 B2 | 10/2012 | Liguore et al. | |
| 8,298,656 B2 | 10/2012 | Schneider | |
| 8,337,654 B2 | 12/2012 | Schmier, II et al. | |
| 8,338,787 B1 | 12/2012 | Shelley et al. | |
| 8,349,105 B2 | 1/2013 | Kehrl et al. | |
| 8,353,348 B2 | 1/2013 | Chitwood et al. | |
| 8,376,275 B2 | 2/2013 | Bolukbasi et al. | |
| 8,383,028 B2 | 2/2013 | Lyons | |
| 8,393,068 B2 | 3/2013 | Keener | |
| 8,409,384 B2 | 4/2013 | Dan-Jumbo et al. | |
| 8,418,962 B2 | 4/2013 | Piehl et al. | |
| 8,419,876 B1 | 4/2013 | Harris | |
| 8,419,887 B2 | 4/2013 | Kennedy | |
| 8,425,708 B2 | 4/2013 | Rubin et al. | |
| 8,430,759 B2 | 4/2013 | Wanthal | |
| 8,431,214 B2 | 4/2013 | Chakrabarti | |
| 8,444,087 B2 | 5/2013 | Kismarton | |
| 8,449,709 B2 | 5/2013 | Modin et al. | |
| 8,465,241 B2 | 6/2013 | Gaw et al. | |
| 8,490,348 B2 | 7/2013 | Wilenski et al. | |
| 8,515,677 B1 * | 8/2013 | Vail | E21B 4/04 264/108 |
| 8,886,388 B2 | 11/2014 | Moser et al. | |
| 2002/0038687 A1 | 4/2002 | Anderson et al. | |
| 2002/0066556 A1 | 6/2002 | Goode et al. | |
| 2002/0157829 A1 | 10/2002 | Davis et al. | |
| 2002/0170711 A1 | 11/2002 | Nuth | |
| 2002/0189806 A1 | 12/2002 | Davidson et al. | |
| 2003/0010491 A1 | 1/2003 | Collette | |
| 2003/0056991 A1 | 3/2003 | Hahn et al. | |
| 2003/0070841 A1 | 4/2003 | Merecka et al. | |
| 2003/0190455 A1 | 10/2003 | Burgess et al. | |
| 2003/0193516 A1 | 10/2003 | Holemans et al. | |
| 2003/0196741 A1 | 10/2003 | Burgess et al. | |
| 2005/0035478 A1 | 2/2005 | Sewell et al. | |
| 2005/0048260 A1 | 3/2005 | Modin et al. | |
| 2005/0059309 A1 | 3/2005 | Tsotsis | |
| 2005/0121094 A1 | 6/2005 | Quigley et al. | |
| 2006/0062650 A1 | 3/2006 | Keener | |
| 2006/0071124 A1 | 4/2006 | Young et al. | |
| 2006/0213250 A1 | 9/2006 | Vaccaro et al. | |
| 2006/0237588 A1 | 10/2006 | Kismarton | |
| 2006/0283133 A1 | 12/2006 | Westre et al. | |
| 2007/0000596 A1 | 1/2007 | Westre et al. | |
| 2007/0022707 A1 | 2/2007 | Gregg et al. | |
| 2007/0089479 A1 | 4/2007 | Vaccaro et al. | |
| 2007/0096751 A1 | 5/2007 | Georgeson et al. | |
| 2007/0107520 A1 | 5/2007 | Vaccaro et al. | |
| 2007/0119256 A1 | 5/2007 | Vaccaro et al. | |
| 2007/0125177 A1 | 6/2007 | Vaccaro et al. | |
| 2008/0054523 A1 | 3/2008 | Hanson | |
| 2008/0121039 A1 | 5/2008 | Vaccaro et al. | |
| 2008/0128078 A1 | 6/2008 | May et al. | |
| 2008/0128430 A1 | 6/2008 | Kovach et al. | |
| 2008/0129041 A1 | 6/2008 | Allen et al. | |
| 2008/0131630 A1 | 6/2008 | Schnelz | |
| 2008/0149343 A1 | 6/2008 | Chitwood | |
| 2008/0196475 A1 | 8/2008 | Engelbart et al. | |
| 2008/0210820 A1 | 9/2008 | Kismarton et al. | |
| 2008/0277057 A1 | 11/2008 | Montgomery et al. | |
| 2008/0277531 A1 | 11/2008 | Ackermann et al. | |
| 2008/0300360 A1 | 12/2008 | Lubowitz et al. | |
| 2009/0004425 A1 | 1/2009 | Lehman et al. | |
| 2009/0019685 A1 | 1/2009 | Keith et al. | |
| 2009/0035510 A1 | 2/2009 | Chakrabarti | |
| 2009/0056109 A1 | 3/2009 | Prichard et al. | |
| 2009/0095413 A1 | 4/2009 | Westre et al. | |
| 2009/0148647 A1 | 6/2009 | Jones et al. | |
| 2009/0181211 A1 | 7/2009 | Lang et al. | |
| 2009/0202767 A1 | 8/2009 | Booker et al. | |
| 2009/0218713 A1 | 9/2009 | Miller et al. | |
| 2009/0226746 A1 | 9/2009 | Chakrabarti et al. | |
| 2009/0261199 A1 | 10/2009 | McCarville et al. | |
| 2009/0263618 A1 | 10/2009 | McCarville et al. | |
| 2009/0317587 A1 | 12/2009 | Deobald et al. | |
| 2010/0011702 A1 | 1/2010 | Wilenski et al. | |
| 2010/0068326 A1 | 3/2010 | Jones et al. | |
| 2010/0074979 A1 | 3/2010 | Cundiff et al. | |
| 2010/0078845 A1 | 4/2010 | Guzman et al. | |
| 2010/0120969 A1 | 5/2010 | Tsotsis | |
| 2010/0133039 A1 | 6/2010 | Liguore | |
| 2010/0187894 A1 | 7/2010 | Kismarton et al. | |
| 2010/0219294 A1 | 9/2010 | Kismarton | |
| 2010/0227106 A1 | 9/2010 | Dan-Jumbo et al. | |
| 2010/0227117 A1 | 9/2010 | Dan-Jumbo et al. | |
| 2010/0233424 A1 | 9/2010 | Dan-Jumbo et al. | |
| 2010/0264266 A1 | 10/2010 | Tsotsis | |
| 2010/0276065 A1 | 11/2010 | Blanchard et al. | |
| 2010/0282904 A1 | 11/2010 | Kismarton et al. | |
| 2010/0319841 A1 | 12/2010 | Rubin et al. | |
| 2010/0320320 A1 | 12/2010 | Kismarton | |
| 2011/0006460 A1 | 1/2011 | Vander Wel et al. | |
| 2011/0045232 A1 | 2/2011 | Kismarton | |
| 2011/0088538 A1 | 4/2011 | Bechtold | |
| 2011/0111172 A1 | 5/2011 | Gideon et al. | |
| 2011/0135887 A1 | 6/2011 | Saff et al. | |
| 2011/0195230 A1 | 8/2011 | Hanson | |
| 2011/0252742 A1 | 10/2011 | Hand et al. | |
| 2011/0262730 A1 | 10/2011 | Tsotsis | |
| 2011/0281114 A1 | 11/2011 | Butler | |
| 2011/0300358 A1 | 12/2011 | Blohowiak et al. | |
| 2011/0311778 A1 | 12/2011 | Burpo et al. | |
| 2011/0315824 A1 | 12/2011 | Pook et al. | |
| 2012/0045606 A1 | 2/2012 | Griess et al. | |
| 2012/0052247 A1 | 3/2012 | Pook et al. | |
| 2012/0052305 A1 | 3/2012 | Weber | |
| 2012/0067513 A1 | 3/2012 | Kismarton et al. | |
| 2012/0067514 A1 | 3/2012 | Hull et al. | |
| 2012/0076989 A1 | 3/2012 | Bland | |
| 2012/0121866 A1 | 5/2012 | Hawkins et al. | |
| 2012/0141705 A1 | 6/2012 | Booker et al. | |
| 2012/0149802 A1 | 6/2012 | Schneider et al. | |
| 2012/0152611 A1 | 6/2012 | Fisher et al. | |
| 2012/0153083 A1 | 6/2012 | Almendros Gomez et al. | |
| 2012/0168071 A1 | 7/2012 | Kennedy et al. | |
| 2012/0171410 A1 | 7/2012 | Darrow et al. | |
| 2012/0193016 A1 | 8/2012 | Saff et al. | |
| 2012/0197482 A1 | 8/2012 | Moser et al. | |
| 2012/0213985 A1 | 8/2012 | Tsotsis | |
| 2012/0223187 A1 | 9/2012 | Kismarton | |
| 2012/0234972 A1 | 9/2012 | Kismarton | |
| 2012/0288664 A1 | 11/2012 | Tsotsis | |
| 2013/0014367 A1 | 1/2013 | Miller et al. | |
| 2013/0014372 A1 | 1/2013 | Miller | |
| 2013/0014378 A1 | 1/2013 | Miller | |
| 2013/0014888 A1 | 1/2013 | Miller et al. | |
| 2013/0014889 A1 | 1/2013 | Miller et al. | |
| 2013/0018499 A1 | 1/2013 | Miller et al. | |
| 2013/0020438 A1 | 1/2013 | Glynn et al. | |
| 2013/0022391 A1 | 1/2013 | Fisher, Jr. et al. | |
| 2013/0034705 A1 | 2/2013 | Matsen et al. | |
| 2013/0036922 A1 | 2/2013 | Stewart et al. | |
| 2013/0047403 A1 | 2/2013 | Gideon et al. | |
| 2013/0056672 A1 | 3/2013 | Johnston et al. | |
| 2013/0075526 A1 | 3/2013 | Griess et al. | |
| 2013/0084434 A1 | 4/2013 | Kehrl et al. | |
| 2013/0087380 A1 | 4/2013 | Dilligan et al. | |
| 2013/0099056 A1 | 4/2013 | Frauen et al. | |
| 2013/0105072 A1 | 5/2013 | Anderson et al. | |
| 2013/0115404 A1 | 5/2013 | Goehlich et al. | |
| 2013/0122236 A1 | 5/2013 | Griess et al. | |
| 2013/0129970 A1 | 5/2013 | Saff et al. | |
| 2013/0149498 A1 | 6/2013 | Wilkerson et al. | |
| 2013/0153145 A1 | 6/2013 | Liguore et al. | |
| 2013/0156979 A1 | 6/2013 | Stewart | |
| 2013/0160923 A1 | 6/2013 | Stehmeiner et al. | |
| 2014/0196953 A1 | 7/2014 | Chitwood et al. | |
| 2015/0344156 A1 | 12/2015 | Vail et al. | |

FOREIGN PATENT DOCUMENTS

| | | |
|---|---|---|
| EP | 1106777 | 6/2001 |
| EP | 1210498 | 6/2002 |
| EP | 1436482 | 7/2004 |

(56) References Cited

FOREIGN PATENT DOCUMENTS

| GB | 2357101 | 6/2001 |
|---|---|---|
| WO | WO 97/08418 | 3/1997 |
| WO | WO 00/28188 | 5/2000 |
| WO | WO 00/50730 | 8/2000 |
| WO | WO 01/12946 | 2/2001 |
| WO | WO 01/48352 | 7/2001 |
| WO | WO 01/94738 | 12/2001 |
| WO | WO 02/29441 | 4/2002 |
| WO | WO 02/086287 | 10/2002 |
| WO | WO 03/016671 | 2/2003 |
| WO | WO 03/036012 | 5/2003 |
| WO | WO 2004/053935 | 6/2004 |
| WO | WO 2004/083595 | 9/2004 |

OTHER PUBLICATIONS

U.S. Appl. No. 14/826,190, filed Aug. 13, 2015, Vail et al.
"About Lock-In Amplifiers," Stanford Research Systems, retrieved from http://www.thinksrs.com/downloads/PDFs/ApplicationNotes/AboutLIAs.pdf, 2004, 9 pages.
"Boeing 787 Dreamliner: a timeline of problems," retrieved from http://www.telegraph.co.uk/travel/travelnews/10207415/Boeing-787-Dreamliner-a-timeline-of-problems.html, 2013, 5 pages.
"JAL 787 in emergency landing in Honolulu after engine oil pressure drops," retrieved from http://uk.news.yahoo.com/jal-787-emergency-landing-honolulu-engine-oil-pressure-111720130--sector.html#RFFsxzK, 2014, 2 pages.
"Japan 787 battery investigators look to latest overheating for clues to earlier meltdown," retrieved from http://finance.yahoo.com/news/japan-787-battery-investigators-look-070825435.html, 2014, 2 pages.
"Lock-in amplifier," retrieved from https://en.wikipedia.org/wiki/Lock-in_amplifier, 2013, 5 pages.
Drew, "New Challenges for the Fixers of Boeing's 787" "The First Big Test of Mending Lightweight Composite Jets," The New York Times, 2013, 5 pages.
"Overheating Dreamliner battery hit 660 Celsius: Japan govt," retrieved from http://news.yahoo.com/overheating-dreamliner-battery-hit-660-celsius-japan-govt-114034948.html, 2014, 1 page.
"Primer on Lithium Ion Battery Technology," NTSB, 2014, 7 pages.
Armen, "Phase sensitive detection: the lock-in amplifier," University of Tennessee, retrieved from http://www.phys.utk.edu/labs/modphys/lock-in%20amplifier%20experiment.pdf, 2008, pp. 1-40.
Baker et al., "Boeing 787-8 Design, Certification, an Manufacturing Systems Review," FAA, 2014, 71 pages.
Columbus, "Ten Ways Cloud Computing is Revolutionizing Aerospace and Defense," retrieved from https://www.aabacosmallbusiness.com/advisor/ten-ways-cloud-computing-revolutionizing-aerospace-defense-022338761.html, 2013, 5 pages.
Gates, "Boeing 787's problems blamed on outsourcing, lack of oversight," Seattle Times, retrieved from http://seattletimes.com/html/businesstechnology/2020275838_boeingoutsourcingxml.html, 2013, 9 pages.
Ghezzo et al., "Onset of Resin Micro-Cracks in Unidirectional Glass Fiber Laminates with Integrated SHM Sensors: Experimental Results," Structural Health Monitoring, 2009, 15 pages.
Hepher, "Airbus drops lithium-ion batteries for A350," Reuters, retrieved from http://www.reuters.com/article/us-airbus-battery-idUSBRE91E07V20130215, 2013, 3 pages.
Irving, "NTSB Thinks the 787 Isn't Safe to Fly," The Daily Beast, 2014, 6 pages.
Jansen, "NTSB urges more tests C739on Boeing 787 Dreamliner batteries," retrieved from http://www.usatoday.com/story/news/nation/2014/05/22/ntsb-dreamliner-boeing-faa-lithium-ion-batteries-united-japan-all-nippon/9433841/, 2014, 4 pages.
Kelly et al., "Boeing 787 grounded in Tokyo for checks after battery vents white smoke," Reuters, 2014, 4 pages.
Koranyi et al., "Boeing says Dreamliner reliability 'better but not satisfactory'," retrieved from http://www.chicagotribune.com/business/sns-rt-us-boeing-dreamliner-20140124,0,1096953.story, 2014, 2 pages.
Kotoky, "India Asks Boeing to Fix Frequent Snags With Dreamliners," retrieved from http://www.bloomberg.com/news/2014-03-03/india-asks-boeing-to-fix-frequent-snags-with-dreamliners.html?cmpid=yhoo, 2014, 2 pages.
Morring, Jr., "Boeing Will Test Composite Cryotanks for NASA," Aerospace Daily, 2011, 2 pages.
Schaper, "Problems Linger for Boeing's Flagship 787 Airliner," retrieved from http://www.npr.org/2014/02/25/282431939/boeings-787-dreaml iner-can-t-shake-major-malfunction-issues, NPR, 2014, 5 pages.
Stoltenberg et al., "The Phase Sensitive (Lock-in) Detector," retrieved from http://courses.washington.edu/phys431/lock-in/lockin.pdf, 2005, pp. 1-21.
Timmerman, "Cryogenic Microcracking of Carbon Fiber/Epoxy Composites: Influences of Fiber-Matrix Adhesion," Journal of Composite Materials, 2003, 1 page, abstract only.
White, "Is the Dreamliner Becoming a Financial Nightmare for Boeing?," retrieved from http://business.time.com/2013/01/17/isthe-dreamliner-becoming-a-financial-nightmare-for-boeing/, 2013, 5 pages.
Wise, "How Airbus Is Debugging the A350," retrieved from http://nybw.businessweek.com/articles/2014-02-13/how-airbus-is-debugging-the-a350, 2014, 9 pages.
Abyzbayev, B.I., et al., "Electrodrilling: Past Experience and Present Opportunities", SPE Paper 38624, 1997 SPE Annual Technical Conference and Exhibition, Oct. 5-8, 1997, pp. 573-588.
Cales, Gerry, et al., "Subsidence Remediation—Extending Well Life Through the Use of Solid Expandable Casing Systems", AADE Paper 01-NC-HO-24, AADE Houston Chapter Mar. 2001 Conference, pp. 1-16.
Coats, E. Alan, et al., "The Hybrid Drilling Unit: An Overview of an Integrated Composite Coiled Tubing and Hydraulic Workover Drilling System", SPE Paper 74349, SPE International Petroleum Conference and Exhibition, Feb. 10-12, 2002, pp. 1-7.
Coats, E. Alan, et al., "The Hybrid Drilling System: Incorporating Composite Coiled Tubing and Hydraulic Workover Technologies into One Integrated Drilling System", IADC/SPE 74538, IADC/SPE Drilling Conference, Feb. 26-28, 2002, pp. 1-7.
Daigle, Chan L., et al., "Expandable Tubulars: Field Examples of Application in Well Construction and Remediation", SPE Paper 62958, SPE Annual Technical Conference and Exhibition, Oct. 1-4, 2000, pp. 1-14.
Denison, E.B., "High Data-Rate Drilling Telemetry System", SPE Paper 6775, Journal of Petroleum Technology, Feb. 1979, pp. 155-163.
Downton, G.C., et al., "Rotary Steerable Drilling System for the 6-in Hole", SPE/IADC 79922, SPE/IADC Drilling Conference, Feb. 19-21, 2003, pp. 1-13.
Dupal, Kenneth K., et al., "Solid Expandable Tubular Technology—A Year of Case Histories in the Drilling Environment", SPE/IADC Paper 67770, SPE/IADC Drilling Conference, Feb. 27-Mar. 1, 2001, pp. 1-16.
Editor, "D2 Deepwater Driller Subsea, All Electric Coil Tubing Exploration System", printed from the website of www.XLTL.com, from the internet, on Aug. 13, 2003, 4 pages.
Filippov, Andrei, et al., "Expandable Tubular Solutions", SPE Paper 56500, 1999 SPE Annual Technical Conference and Exhibition, Oct. 3-6, 1999, pp. 1-6.
Cohan "Is Boeing's 787 safe to fly?" Daily Finance, Jun. 24, 2009, 4 pages (found at http://www.dailyfinance.com/2009/06/24/is-boeing-s-787-safe-to-fly/).
Gates "Double trouble for Boeing 787 wing; Damage from design flaw extends into jet body; Problems surfaced at stress levels short of certification standard." The Seattle Times, Jul. 30, 2009, 1 page.
Gates "Months of delay likely for 787, Boeing partner says," The Seattle Times, Jun. 25, 2009, 3 pages.

(56) References Cited

OTHER PUBLICATIONS

Head, P.F., et al., "Electric Coiled Tubing Drilling—The First Steps toward a Smart CT Drilling System", SPE Paper 46013, 1998 SPE-ICoTA Coiled Tubing Roundtable, Apr. 15-16, 1998, pp. 61-70.

Head, Phil, et al., "Intelligent Coiled Tubing Joint Industry Project", SPE Paper 60712, 2000 SPE/ICoTA Coiled Tubing Roundtable, Apr. 5-6, 2000, pp. 1-7.

Head, Philip, et al., "Electric Coiled Tubing Drilling (E-CTD) Project Update", SPE Paper 68441, SPE/ICoTA Coiled Tubing Roundtable, Mar. 7-8, 2001, pp. 1-9.

Head, Philip, et al., "Intelligent Coiled Tubing (ICT) for Completions and Flowlines", SPE Paper 68357, 2001 SPE/ICoTA Coiled Tubing Roundtable, Mar. 7-8, 2001, pp. 1-4.

Kamp, G.P., et al., "Development of a Power and Data Transmission Thermoplastic Composite Coiled Tubing for Electric Drilling", SPE Paper 60730, 2000 SPE/ICoTA Coiled Tubing Roundtable, Apr. 5-6, 2000, pp. 1-7.

Leising, L.J., et al., "Extending the Reach of Coiled Tubing Drilling (Thrusters, Equalizers and Tractors)", SPE/IADC Paper 37656, 1997 SPE/IADC Drilling Conference, Mar. 4-6, 1997, pp. 677-690.

Lohoefer, C. Lee, et al., "Expandable Liner Hanger Provides Cost-Effective Alternative Solution", IADC/SPE paper 59151, 2000 IADC/SPE Drilling Conference, Feb. 23-25, 2000, pp. 1-12.

Lurie, Paul, et al., "Smart Drilling with Electric Drillstring™", SPE/IADC Paper 79886, SPE/IADC Drilling Conference, Feb. 19-21, 2003, pp. 1-13.

Maranuk, C.A., et al., "A Concept of a New Steerable Drilling System for Coiled Tubing", SPE Paper 60752, 2000 SPE/ICoTA Coiled Tubing Roundtable, Apr. 5-6, 2000, pp. 1-10.

Marker, Roy, et al., "Anaconda: Joint Development Project Leads to Digitally Controlled Composite Coiled Tubing Drilling System", SPE Paper 60750, SPE/ICoTA Coiled Tubing Roundtable, Apr. 5-6, 2000, pp. 1-9.

Ohlinger, James J., et al., "A Comparison of Mud Pulse and E-Line Telemetry in Alaska CTD Operations", SPE Paper 74842, SPE/ICoTA Coiled Tubing Conference and Exhibition, Apr. 9-10, 2002, pp. 1-5.

Pavone, D.R., et al., "Application of High Sampling Rate Downhole Measurements for Analysis and Cure of Stick-Slip in Drilling", SPE Paper 28324, SPE 69th Annual Conference Technical and Exhibition, Sep. 25-28, 1994, pp. 335-345.

Rixse, Mel, et al., "High Performance Coil Tubing Drilling in Shallow North Slope Heavy Oil", IADC/SPE Paper 74553, IADC/SPE Drilling Conference, Feb. 26-28, 2002, pp. 1-10.

Sanchez, Alfredo, et al., "An Approach for the Selection and Design of Slim Downhole Motors for Coiled Tubing Drilling", SPE Paper 37054, 1996 SPE Horizontal Drilling Conference, Nov. 18-20, 1996, pp. 197-205.

Sarapuu, Erich, "Electrical Disintegrating Drilling", SPE Paper 300, 1962 Production Research Symposium, Apr. 12-13, 1962, pp. 201-206.

Sas-Jaworsky, Alexander, et al., "Development of Composite Coiled Tubing for Oilfield Services", SPE Paper 26536, 68th Annual Technical Conference and Exhibition, Oct. 3-6, 1993, pp. 1-15.

Sawaryn, S.J., "The Dynamics of Electric Submersible Pump Populations and the Implication for Dual ESP Systems", SPE Paper 63043, 2000 SPE Annual Technical Conference and Exhibition, Oct. 1-4, 2000, pp. 1-16.

Selby, Bruce, et al., "Hybrid Coiled Tubing System for Offshore Re-entry Drilling and Workover", IADC/SPE Paper 39374, 1998 IADC/SPE Drilling Conference, Mar. 3-6, 1998, pp. 711-721.

Shepard, S.F., et al., "Casing Drilling: An Emerging Technology", IADC/SPE Paper 67731, 2001 SPE/IADC Drilling Conference, Feb. 27-Mar. 1, 2001, pp. 1-13.

Tinkham, Scott K., et al., "Wired BHA Applications in Underbalanced Coiled Tubing Drilling", IADC/SPE Paper 59161, 2000 IADC/SPE Drilling Conference, Feb. 23-25, 2000, pp. 1-13.

Turner, D.R., et al., "Electric Coiled Tubing Drilling: A Smarter CT Drilling System", SPE/IADC Paper 52791, 1999 SPE/IADC Drilling Conference, Mar. 9-11, 1999, pp. 1-13.

Turner, Daniel R., et al., "The All Electric BHA: Recent Developments towards an Intelligent Coiled-Tubing Drilling System", SPE Paper 54469, 1999 SPE/ICoTA Coiled Tubing Roundtable, May 25-26, 1999, pp. 1-10.

Turner, Dan, et al., "New D.C. Motor for Downhole Drilling and Pumping Applications", SPE Paper 68489, SPE/ICoTA Coiled Tubing Roundtable, Mar. 7-8, 2001, pp. 1-7.

Warren, Tommy M., et al., "Casing Drilling Application Design Considerations", IADC/SPE Paper 59179, 2000 IADC/SPE Drilling Conference, Feb. 23-25, 2000, pp. 1-11.

Official Action for U.S. Appl. No. 10/223,025, mailed Dec. 15, 2003.

Notice of Allowance for U.S. Appl. No. 10/223,025, mailed Aug. 6, 2004.

Official Action for U.S. Appl. No. 10/729,509, mailed Dec. 15, 2004.

Official Action for U.S. Appl. No. 10/729,509, mailed Jul. 14, 2005.

Notice of Allowance for U.S. Appl. No. 10/729,509, mailed Oct. 14, 2005.

Official Action for U.S. Appl. No. 10/800,443, mailed Jan. 17, 2006.
Official Action for U.S. Appl. No. 10/800,443, mailed Jun. 6, 2005.
Official Action for U.S. Appl. No. 10/800,443, mailed Sep. 8, 2006.
Official Action for U.S. Appl. No. 10/800,443, mailed Apr. 6, 2007.
Notice of Allowance for U.S. Appl. No. 10/800,443, mailed Aug. 27, 2007.

Official Action for U.S. Appl. No. 12/005,105, mailed Jan. 26, 2009.
Official Action for U.S. Appl. No. 12/005,105, mailed Nov. 20, 2009.

Official Action for U.S. Appl. No. 12/005,105, mailed Nov. 26, 2010.

Official Action for U.S. Appl. No. 12/583,240, mailed Dec. 5, 2011, 10 pages.

Notice of Allowance for U.S. Appl. No. 12/583,240, mailed Aug. 20, 2012, 7 pages.

Official Action for U.S. Appl. No. 12/804,039, mailed Oct. 3, 2012 12 pages.

Notice of Allowance for U.S. Appl. No. 12/804,039, mailed Apr. 12, 2013, 11 pages.

Hsu, "Nondestructive Inspection of Composite Structures: Methods and Practice," 17th World Conference on Nondestructive Testing, 2008, 14 pages.

Williams, Offshore oil composites: Designing in cost savings, High-Performance Composites, 2009, 3 pages.

Yu, "Signs of pre-existing fatigue found on Southwest aircraft," USA Today, 2011, 3 pages.

Crossley et al., "Smart Patches: Self-monitoring composite patches for the repair of aircraft," Proceedings of SPIE, 2004, vol. 5275, pp. 304-315.

Smith et al., "Fabrication of woven carbon fibre/polycarbonate repair patches," Composites Part A, 1996, vol. 27A, pp. 1089-1095.

Takeda et al., "Debonding monitoring of composite repair patches using embedded small-diameter FBG sensors," Smart Materials and Structures, 2007, vol. 16, pp. 763-770.

Official Action for U.S. Appl. No. 14/167,766, mailed Apr. 19, 2016, 11 pages.

Notice of Allowance for U.S. Appl. No. 14/167,766, mailed Oct. 26, 2016, 5 pages.

* cited by examiner

METHODS AND APPARATUS TO PREVENT FAILURES OF FIBER-REINFORCED COMPOSITE MATERIALS UNDER COMPRESSIVE STRESSES CAUSED BY FLUIDS AND GASES INVADING MICROFRACTURES IN THE MATERIALS

PRIORITY FROM RECENT U.S. PROVISIONAL PATENT APPLICATIONS

Applicant claims priority for this application to U.S. Provisional Patent Application Ser. No. 61/849,968, filed on Feb. 6, 2013, that is entitled "Additional Methods and Apparatus to Prevent Failures of Fiber-Reinforced Composite Materials Under Compressive Stresses Caused by Fluids and Gases Invading Microfractures in Materials", an entire copy of which is incorporated herein by reference. (PPA-34)

Applicant claims priority for this application to U.S. Provisional Patent Application Ser. No. 61/849,585, filed on Jan. 29, 2013, that is entitled "Proposed Modifications of Main and APU Lithium-Ion Battery Assemblies on the Boeing 787 to Prevent Fires: Add One Cell, Eliminate Groundloops, and Monitor Each Cell with Optically Isolated Electronics", an entire copy of which is incorporated herein by reference. (PPA-101)

Applicant claims priority for this application to U.S. Provisional Patent Application Ser. No. 61/850,095, filed on Feb. 9, 2013, that is entitled "Proposed Modifications of Main and APU Lithium-Ion Battery Assemblies on the Boeing 787 to Prevent Fires: Add One Cell, Eliminate Groundloops, and Monitor Each Cell with Optically Isolated Electronics—Part 2", an entire copy of which is incorporated herein by reference. (PPA-102)

Applicant also claims priority for this application to U.S. Provisional Patent Application Ser. No. 61/850,774, filed on Feb. 22, 2013, that is entitled "Proposed Modifications of Main and APU Lithium-Ion Battery Assemblies on the Boeing 787 to Prevent Fires: Add One Cell, Eliminate Groundloops, and Monitor Each Cell with Optically Isolated Electronics—Part 3", an entire copy of which is incorporated herein by reference. (PPA-103)

PRIORITY FROM A CO-PENDING U.S. PATENT APPLICATION

The present application is a continuation-in-part (C.I.P) application of co-pending U.S. patent application Ser. No. 12/804,039, filed on Jul. 12, 2010, that is entitled "Methods and Apparatus to Prevent Failures of Fiber-Reinforced Composite Materials Under Compressive Stresses Caused by Fluids and Gases Invading Microfractures in the Materials", an entire copy of which is incorporated herein by reference. Applicant claims priority to this co-pending U.S. patent application Ser. No. 12/804,039 filed on Jul. 12, 2010. (Composite-1)

Co-pending U.S. patent application Ser. No. 12/804,039 claimed priority to U.S. Provisional Patent Application No. 61/270,709, filed Jul. 10, 2009, that is entitled "Methods and Apparatus to Prevent Failures of Fiber-Reinforced Composite Materials Under Compressive Stresses Caused by Fluids and Gases Invading Microfractures in the Materials", an entire copy of which is incorporated herein by reference. Applicant claims priority to this U.S. Provisional Patent Application No. 61/270,709, filed Jul. 10, 2009. (PPA-32)

Co-pending U.S. patent application Ser. No. 12/804,039 claimed priority to U.S. Provisional Patent Application No. 61/396,518, filed on May 29, 2010, that is entitled "Letter to Boeing Management", an entire copy of which is incorporated herein by reference. Applicant claims priority to this U.S. Provisional Patent Application No. 61/396,518, filed May 29, 2010. (PPA-33)

PRIORITY FROM PREVIOUS U.S. PATENT APPLICATIONS

Co-pending U.S. patent application Ser. No. 12/804,039 is a continuation-in-part (C.I.P.) application of U.S. patent application Ser. No. 12/583,240, filed on Aug. 17, 2009, that is entitled "High Power Umbilicals for Subterranean Electric Drilling Machines and Remotely Operated Vehicles", an entire copy of which is incorporated herein by reference. Ser. No. 12/583,240 was published on Dec. 17, 2009 having Publication Number US 2009/0308656 A1, an entire copy of which is incorporated herein by reference. Ser. No. 12/583, 240 issued as U.S. Pat. No. 8,353,348 B2 on Jan. 15, 2013, an entire copy of which is incorporated herein by reference. Applicant claims priority to this U.S. Patent Application Ser. No. 12/583,240. (Rig-5)

Ser. No. 12/583,240 is a continuation-in-part (C.I.P.) application of U.S. patent application Ser. No. 12/005,105, filed on Dec. 22, 2007, that is entitled "High Power Umbilicals for Electric Flowline Immersion Heating of Produced Hydrocarbons", an entire copy of which is incorporated herein by reference. Ser. No. 12/005,105 was published on Jun. 26, 2008 having Publication Number US 2008/0149343 A1, an entire copy of which is incorporated herein by reference. Ser. No. 12/005,105 is now abandoned. Applicant claims priority to this U.S. patent application Ser. No. 12/005,105. (Rig-4)

Ser. No. 12/005,105 a continuation-in-part (C.I.P.) application of U.S. patent application Ser. No. 10/800,443, filed on Mar. 14, 2004, that is entitled "Substantially Neutrally Buoyant and Positively Buoyant Electrically Heated Flowlines for Production of Subsea Hydrocarbons", an entire copy of which is incorporated herein by reference. Ser. No. 10/800,443 was published on Dec. 9, 2004 having Publication Number US 2004/0244982 A1, an entire copy of which is incorporated herein by reference. Ser. No. 10/800,443 issued as U.S. Pat. No. 7,311,151 B2 on Dec. 25, 2007. Applicant claims priority to this U.S. patent application Ser. No. 10/800,443. (Rig-3)

Ser. No. 10/800,443 claimed priority from U.S. Provisional Patent Applications No. 60/455,657, No. 60/504,359, No. 60/523,894, No. 60/532,023, and No. 60/535,395. Applicant claims priority in the present application to these five Provisional Patent Applications, and an entire copy of each is incorporated herein by reference.

Ser. No. 10/800,443 is a continuation-in-part (C.I.P.) application of U.S. patent application Ser. No. 10/729,509, filed on Dec. 4, 2003, that is entitled "High Power Umbilicals for Electric Flowline Immersion Heating of Produced Hydrocarbons", an entire copy of which is incorporated herein by reference. Ser. No. 10/729,509 was published on Jul. 15, 2004 having the Publication Number US 2004/ 0134662 A1, an entire copy of which is incorporated herein by reference. Ser. No. 10/729,509 issued as U.S. Pat. No. 7,032,658 B2 on Apr. 25, 2006, an entire copy of which is incorporated herein by reference. Applicant claims priority to this U.S. patent application Ser. No. 10/729,509. (Rig-2)

Ser. No. 10/729,509 claimed priority from various Provisional Patent Applications, including Provisional Patent Application Nos. 60/432,045, 60/523,894, 60/504359, 60/455,657 and 60/448,191. Applicant claims priority in the present application to these five Provisional Patent Applications, and an entire copy of each is incorporated herein by reference.

Ser. No. 10/729,509 is a continuation-in-part (C.I.P) application of U.S. patent application Ser. No. 10/223,025, filed Aug. 15, 2002, that is entitled "High Power Umbilicals for Subterranean Electric Drilling Machines and Remotely Operated Vehicles", an entire copy of which is incorporated herein by reference. Ser. No. 10/223,025 was published on Feb. 20, 2003, having Publication Number US 2003/0034177 A1, an entire copy of which is incorporated herein by reference. Ser. No. 10/223,025 issued as U.S. Pat. No. 6,857,486 B2 on Feb. 22, 2005, an entire copy of which is incorporated herein by reference. Applicant claims priority to this U.S. patent application Ser. No. 10/223,025. (Rig-1)

A RELATED CO-PENDING U.S. PATENT APPLICATION

Co-pending U.S. patent application Ser. No. 13/694,884, filed on Jan. 15, 2013, is a continuation-in-part (C.I.P.) application of U.S. patent application Ser. No. 12/583,240, filed on Aug. 17, 2009, that is entitled "High Power Umbilicals for Subterranean Electric Drilling Machines and Remotely Operated Vehicles", an entire copy of which is incorporated herein by reference. Applicant does not claim priority to this co-pending U.S. patent application Ser. No. 13/694,884, filed on Jan. 15, 2013. (Rig-7)

CROSS-REFERENCES TO RELATED APPLICATIONS

This application relates to Provisional Patent Application No. 60/313,654 filed on Aug. 19, 2001, that is entitled "Smart Shuttle Systems", an entire copy of which is incorporated herein by reference.

This application relates to Provisional Patent Application No. 60/353,457 filed on Jan. 31, 2002, that is entitled "Additional Smart Shuttle Systems", an entire copy of which is incorporated herein by reference.

This application relates to Provisional Patent Application No. 60/367,638 filed on Mar. 26, 2002, that is entitled "Smart Shuttle Systems and Drilling Systems", an entire copy of which is incorporated herein by reference.

This application relates to Provisional Patent Application No. 60/384,964 filed on Jun. 3, 2002, that is entitled "Umbilicals for Well Conveyance Systems and Additional Smart Shuttles and Related Drilling Systems", an entire copy of which is incorporated herein by reference.

This application relates to Provisional Patent Application No. 60/432,045, filed on Dec. 8, 2002, that is entitled "Pump Down Cement Float Valves for Casing Drilling, Pump Down Electrical Umbilicals, and Subterranean Electric Drilling Systems", an entire copy of which is incorporated herein by reference.

This application relates to Provisional Patent Application No. 60/448,191, filed on Feb. 18, 2003, that is entitled "Long Immersion Heater Systems", an entire copy of which is incorporated herein by reference.

This application relates to Provisional Patent Application No. 60/455,657, filed on Mar. 18, 2003, that is entitled "Four SDCI Application Notes Concerning Subsea Umbilicals and Construction Systems", an entire copy of which is incorporated herein by reference.

This application relates to Provisional Patent Application No. 60/504,359, filed on Sep. 20, 2003, that is entitled "Additional Disclosure on Long Immersion Heater Systems", an entire copy of which is incorporated herein by reference.

This application relates to Provisional Patent Application No. 60/523,894, filed on Nov. 20, 2003, that is entitled "More Disclosure on Long Immersion Heater Systems", an entire copy of which is incorporated herein by reference.

This application relates to Provisional Patent Application No. 60/532,023, filed on Dec. 22, 2003, that is entitled "Neutrally Buoyant Flowlines for Subsea Oil and Gas Production", an entire copy of which is incorporated herein by reference.

This application relates to Provisional Patent Application No. 60/535,395, filed on Jan. 10, 2004, that is entitled "Additional Disclosure on Smart Shuttles and Subterranean Electric Drilling Machines", an entire copy of which is incorporated herein by reference.

This application relates to Provisional Patent Application No. 60/661,972, filed on Mar. 14, 2005, that is entitled "Electrically Heated Pumping Systems Disposed in Cased Wells, in Risers, and in Flowlines for Immersion Heating of Produced Hydrocarbons", an entire copy of which is incorporated herein by reference.

This application relates to Provisional Patent Application No. 60/665,689, filed on Mar. 28, 2005, that is entitled "Automated Monitoring and Control of Electrically Heated Pumping Systems Disposed in Cased Wells, in Risers, and in Flowlines for Immersion Heating of Produced Hydrocarbons", an entire copy of which is incorporated herein by reference.

This application relates to Provisional Patent Application No. 60/669,940, filed on Apr. 9, 2005, that is entitled "Methods and Apparatus to Enhance Performance of Smart Shuttles and Well Locomotives", an entire copy of which is incorporated herein by reference.

This application relates to Provisional Patent Application No. 60/761,183, filed on Jan. 23, 2006, that is entitled "Methods and Apparatus to Pump Wirelines into Cased Wells Which Cause No Reverse Flow", an entire copy of which is incorporated herein by reference.

This application relates to Provisional Patent Application No. 60/794,647, filed on Apr. 24, 2006, that is entitled "Downhole DC to AC Converters to Power Downhole AC Electric Motors and Other Methods to Send Power Downhole", an entire copy of which is incorporated herein by reference.

RELATED U.S. APPLICATIONS

The following applications are related to this application, but applicant does not claim priority from the following related applications.

This application relates to Ser. No. 09/375,479, filed Aug. 16, 1999, having the title of "Smart Shuttles to Complete Oil and Gas Wells", that issued on Feb. 20, 2001, as U.S. Pat. No. 6,189,621 B1, an entire copy of which is incorporated herein by reference.

This application relates to Ser. No. 09/487,197, filed Jan. 19, 2000, having the title of "Closed-Loop System to Complete Oil and Gas Wells", that issued on Jun. 4, 2002 as U.S. Pat. No. 6,397,946 B1, an entire copy of which is incorporated herein by reference.

This application relates to application Ser. No. 10/162,302, filed Jun. 4, 2002, having the title of "Closed-Loop Conveyance Systems for Well Servicing", that issued as U.S. Pat. No. 6,868,906 B1 on Mar. 22, 2005, an entire copy of which is incorporated herein by reference.

This application relates to application Ser. No. 11/491,408, filed Jul. 22, 2006, having the title of "Methods and Apparatus to Convey Electrical Pumping Systems into Wellbores to Complete Oil and Gas Wells", that issued as U.S. Pat. No. 7,325,606 B1 on Feb. 5, 2008, an entire copy of which is incorporated herein by reference.

This application relates to application Ser. No. 12/012,822, filed Feb. 5, 2008, having the title of "Methods and Apparatus to Convey Electrical Pumping Systems into Wellbores to Complete Oil and Gas Wells", that issued as U.S. Pat. No. 7,836,950 B2 on Nov. 23, 2010, an entire copy of which is incorporated herein by reference.

RELATED FOREIGN APPLICATIONS

This application also relates to PCT Application Serial Number PCT/US00/22095, filed Aug. 9, 2000, having the title of "Smart Shuttles to Complete Oil and Gas Wells", that has International Publication Number WO 01/12946 A1, that has International Publication Date of Feb. 22, 2001, that issued as European Patent No. 1,210,498 B1 on Nov. 28, 2007, an entire copy of which is incorporated herein by reference.

This application relates to PCT Patent Application Number PCT/US02/26066 filed on Aug. 16, 2002, entitled "High Power Umbilicals for Subterranean Electric Drilling Machines and Remotely Operated Vehicles", that has the International Publication Number WO 03/016671 A2, that has International Publication Date of Feb. 27, 2003, that issued as European Patent No. 1,436,482 B1 on Apr. 18, 2007, an entire copy of which is incorporated herein by reference.

This application relates to PCT Patent Application Number PCT/US03/38615 filed on Dec. 5, 2003, entitled "High Power Umbilicals for Electric Flowline Immersion Heating of Produced Hydrocarbons", that has the International Publication Number WO 2004/053935 A2, that has International Publication Date of Jun. 24, 2004, an entire copy of which is incorporated herein by reference.

This application relates to PCT Patent Application Number PCT/US2004/008292, filed on Mar. 17, 2004, entitled "Substantially Neutrally Buoyant and Positively Buoyant Electrically Heated Flowlines for Production of Subsea hydrocarbons", that has International Publication Number WO 2004/083595 A2 that has International Publication Date of Sep. 30, 2004, an entire copy of which is incorporated herein by reference.

RELATED U.S. DISCLOSURE DOCUMENTS

This application relates to disclosure in U.S. Disclosure Document No. 451,044, filed on Feb. 8, 1999, that is entitled 'RE: —Invention Disclosure—"Drill Bit Having Monitors and Controlled Actuators", an entire copy of which is incorporated herein by reference.

This application relates to disclosure in U.S. Disclosure Document No. 458,978 filed on Jul. 13, 1999 that is entitled in part "RE: —INVENTION DISCLOSURE MAILED Jul. 13, 1999", an entire copy of which is incorporated herein by reference.

This application relates to disclosure in U.S. Disclosure Document No. 475,681 filed on Jun. 17, 2000 that is entitled in part "ROV Conveyed Smart Shuttle System Deployed by Workover Ship for Subsea Well Completion and Subsea Well Servicing", an entire copy of which is incorporated herein by reference.

This application relates to disclosure in U.S. Disclosure Document No. 496,050 filed on Jun. 25, 2001 that is entitled in part "SDCI Drilling and Completion Patents and Technology and SDCI Subsea Re-Entry Patents and Technology", an entire copy of which is incorporated herein by reference.

This application relates to disclosure in U.S. Disclosure Document No. 480,550 filed on Oct. 2, 2000 that is entitled in part "New Draft Figures for New Patent Applications", an entire copy of which is incorporated herein by reference.

This application relates to disclosure in U.S. Disclosure Document No. 493,141 filed on May 2, 2001 that is entitled in part "Casing Boring Machine with Rotating Casing to Prevent Sticking Using a Rotary Rig", an entire copy of which is incorporated herein by reference.

This application relates to disclosure in U.S. Disclosure Document No. 492,112 filed on Apr. 12, 2001 that is entitled in part "Smart Shuttle™ Conveyed Drilling Systems", an entire copy of which is incorporated herein by reference.

This application relates to disclosure in U.S. Disclosure Document No. 495,112 filed on Jun. 11, 2001 that is entitled in part "Liner/Drainhole Drilling Machine", an entire copy of which is incorporated herein by reference.

This application relates to disclosure in U.S. Disclosure Document No. 494,374 filed on May 26, 2001 that is entitled in part "Continuous Casting Boring Machine", an entire copy of which is incorporated herein by reference.

This application relates to disclosure in U.S. Disclosure Document No. 495,111 filed on Jun. 11, 2001 that is entitled in part "Synchronous Motor Injector System", an entire copy of which is incorporated herein by reference.

This application relates to disclosure in U.S. Disclosure Document No. 497,719 filed on Jul. 27, 2001 that is entitled in part "Many Uses for The Smart Shuttle™ and Well Locomotive™", an entire copy of which is incorporated herein by reference.

This application relates to disclosure in U.S. Disclosure Document No. 498,720 filed on Aug. 17, 2001 that is entitled in part "Electric Motor Powered Rock Drill Bit Having Inner and Outer Counter-Rotating Cutters and Having Expandable/Retractable Outer Cutters to Drill Boreholes into Geological Formations", an entire copy of which is incorporated herein by reference.

This application relates to disclosure in U.S. Disclosure Document No. 499,136 filed on Aug. 26, 2001, that is entitled in part "Commercial System Specification PCP-ESP Power Section for Cased Hole Internal Conveyance Large Well Locomotive™", an entire copy of which is incorporated herein by reference.

This application relates to disclosure in U.S. Disclosure Document No. 516,982 filed on Aug. 20, 2002, that is entitled "Feedback Control of RPM and Voltage of Surface Supply", an entire copy of which is incorporated herein by reference.

This application relates to disclosure in U.S. Disclosure Document No. 531,687 filed May 18, 2003, that is entitled "Specific Embodiments of Several SDCI Inventions", an entire copy of which is incorporated herein by reference.

This application relates to U.S. Disclosure Document No. 572,723, filed on Mar. 14, 2005, that is entitled "Electrically Heated Pumping Systems Disposed in Cased Wells, in Risers, and in Flowlines for Immersion Heating of Produced Hydrocarbons", an entire copy of which is incorporated herein by reference.

This application relates to U.S. Disclosure Document No. 573,813, filed on Mar. 28, 2005, that is entitled "Automated Monitoring and Control of Electrically Heated Pumping Systems Disposed in Cased Wells, in Risers, and in Flowlines for Immersion Heating of Produced Hydrocarbons", an entire copy of which is incorporated herein by reference.

This application relates to U.S. Disclosure Document No. 574,647, filed on Apr. 9, 2005, that is entitled "Methods and Apparatus to Enhance Performance of Smart Shuttles and Well Locomotives", an entire copy of which is incorporated herein by reference.

This application relates to U.S. Disclosure Document No. 593,724, filed Jan. 23, 2006, that is entitled "Methods and Apparatus to Pump Wirelines into Cased Wells Which Cause No Reverse Flow", an entire copy of which is incorporated herein by reference.

This application relates to U.S. Disclosure Document No. 595,322, filed Feb. 14, 2006, that is entitled "Additional Methods and Apparatus to Pump Wirelines into Cased Wells Which Cause No Reverse Flow", an entire copy of which is incorporated herein by reference.

This application relates to U.S. Disclosure Document No. 599,602, filed on Apr. 24, 2006, that is entitled "Downhole DC to AC Converters to Power Downhole AC Electric Motors and Other Methods to Send Power Downhole", an entire copy of which is incorporated herein by reference.

This application relates to the U.S. Disclosure Document that is entitled "Seals for Smart Shuttles" that was mailed to the USPTO on the Date of Dec. 22, 2006 by U.S. Mail, Express Mail Service having Express Mail Number EO 928 739 065 US, an entire copy of which is incorporated herein by reference.

Various references are referred to in the above defined U.S. Disclosure Documents. For the purposes herein, the term "reference cited in applicant's U.S. Disclosure Documents" shall mean those particular references that have been explicitly listed and/or defined in any of applicant's above listed U.S. Disclosure Documents and/or in the attachments filed with those U.S. Disclosure Documents. Applicant explicitly includes herein by reference entire copies of each and every "reference cited in applicant's U.S. Disclosure Documents". In particular, applicant includes herein by reference entire copies of each and every U.S. Patent cited in U.S. Disclosure Document No. 452648, including all its attachments, that was filed on Mar. 5, 1999. To best knowledge of applicant, all copies of U.S. Patents that were ordered from commercial sources that were specified in the U.S. Disclosure Documents are in the possession of applicant at the time of the filing of the application herein.

RELATED U.S. TRADEMARKS

Applications for U.S. Trademarks have been filed in the USPTO for several terms used in this application. An application for the Trademark "Smart Shuttle™" was filed on Feb. 14, 2001 that is Ser. No. 76/213,676, an entire copy of which is incorporated herein by reference. The term Smart Shuttle® is now a Registered Trademark. The "Smart Shuttle™ is also called the "Well Locomotive™ ". An application for the Trademark "Well Locomotive™" was filed on Feb. 20, 2001 that is Ser. No. 76/218,211, an entire copy of which is incorporated herein by reference. The term Well Locomotive® is now a Registered Trademark. An application for the Trademark of "Downhole Rig™" was filed on Jun. 11, 2001 that is Ser. No. 76/274,726, an entire copy of which is incorporated herein by reference. An application for the Trademark "Universal Completion Device™" was filed on Jul. 24, 2001 that is Ser. No. 76/293,175, an entire copy of which is incorporated herein by reference. An application for the Trademark "Downhole BOP™" was filed on Aug. 17, 2001 that is Ser. No. 76/305,201, an entire copy of which is incorporated herein by reference.

Accordingly, in view of the Trademark registrations and applications, the term "smart shuttle" is capitalized as "Smart Shuttle"; the term "well locomotive" is capitalized as "Well Locomotive"; the term "downhole rig" is capitalized as "Downhole Rig"; the term "universal completion device" is capitalized as "Universal Completion Device"; and the term "downhole bop" is capitalized as "Downhole BOP".

In addition, the following Trademarks are also used herein: "Subterranean Electric Drilling Machine™" abbreviated "SEDM™.

BACKGROUND OF THE INVENTION

Field of the Invention

The field of invention relates to methods and apparatus to prevent failures of fiber-reinforced composite materials under compressive stresses caused by fluids and gases invading microfractures in those materials.

Description of the Related Art

Catastrophic failures of fiber-reinforced composite materials have proven to be a problem in the oil and gas industries. Now, such fiber-reinforced composite materials have now been incorporated into critically important structural components of aircraft. Such structural components include but are not limited to the wing and the wing junction boxes of aircraft. Any catastrophic failure of fiber-reinforced wings and/or wing junction boxes or other structural components during flight would likely result in significant loss of life and the destruction of the aircraft.

A problem with composites is that they catastrophically delaminate under certain circumstances. For example please refer to the article entitled "Offshore oil composites: Designing in cost savings" by Dr. Jerry Williams, a copy of which appears in Attachment No. 3 to U.S. Provisional Patent Application No. 61/270,709, filed on Jul. 10, 2009, an entire copy of which is incorporated herein by reference. One notable quote is as follows: " . . . (the) failure modes are different for metals and composites: Compression failure modes for composites include delamination and shear crippling that involves microbuckling of the fibers."

Based upon Dr. Williams' assessments, clearly compressive forces applied to composites can cause significant problems. Carbon fiber filaments are typically woven into a fabric material, which may be typically impregnated with epoxy resin. Such structures are then typically laminated and cured. On a microscopic level, and in compression, the carbon fibers can buckle. This in turn opens up what the applicant herein calls "microfractures" (or "microcracks") in larger fabricated parts which are consequently subject to invasion by fluids and gasses.

Because of the risk of catastrophic delamination of composites under compression, our firm, Smart Drilling and Completion, Inc., decided some time ago to use titanium or aluminum interior strength elements, and to surround these materials with fiber-reinforced composite materials to make certain varieties of umbilicals. For example, please see FIGS. 1A, 1B, and 1C in the U.S. Patent Application entitled "High Power Umbilicals for Subterranean Electric Drilling Machines and Remotely Operated Vehicles", that is Ser. No. 12/583,240, filed Aug. 17, 2009, that was published on Dec. 17, 2009 as US 2009/038656 A1, an entire copy of which is incorporated herein by reference. Perhaps our firm will also include embedded syntactic foam materials so that the fabricated umbilicals are neutrally buoyant in typical drilling muds for its intended use in a borehole.

Reference is made to the front-page article in The Seattle Times dated Jun. 25, 2009 entitled "787 delay: months, not weeks", an entire copy of which is incorporated herein by reference. This article states in part, under the title of "Last months: test" the following: "This test produced delamination of the composite material—separation of the carbon-fiber layers, in small areas where the MHI wings join the structure box embedded in the center fuselage made by Fugi Heavy Industries (FHI) of Japan." It should certainly be no news to those of at least ordinary skill in the art that this is a high stress area, and portions of these stresses will inevitably be compressive in nature.

Consequently, in such areas subject to compressive stresses, microfractures will allow, for example, water, water vapor, fuel, grease, fuel vapor, and vapors from burned jet fuel to enter these microfractures, that in turn, could cause a catastrophic failure of the wing and/or the wing junction box—possibly during flight. Similar catastrophic problems could arise at other locations including composite materials.

The counter-argument can be presented as follows: "but, the military flies aircraft made from these materials all the time, and there is no problem". Yes, but, the military often keeps their planes in hangers, has many flight engineers regularly and continuously inspecting them, and suitably recoats necessary surfaces with many chemicals to protect the composites and to patch radar absorbing stealth materials. So, it may not be wise to extrapolate the "no problems in the military argument" to the exposure of wings and wing boxes in civil commercial aircraft, including those of the 787, to at least some substantial repetitive compressive forces that may also be simultaneously subject to long-term environmental contamination by ambient fluids and gases.

Reference is also made to the Jun. 24, 2009 summary article in the Daily Finance entitled "Is Boeing's 787 safe to fly"?, by Peter Cohan, the one page summary copy of which appears in Attachment No. 4 to U.S. Provisional Patent Application No. 61/270,709 filed on Jul. 10, 2009, an entire copy of which is incorporated herein by reference. This article states in part: "Composites are lighter and stronger hence able to fly more fuel efficiently. But engineers don't completely understand how aircraft made of composite materials will respond to the stresses of actual flight. This incomplete understanding is reflected in the computer models they use to design the aircraft. The reason for the fifth delay is that the actual 787 did not behave the way the model predicted."

The complete article entitled "Is Boeing's 787 safe to fly?", in the Daily Finance, by Peter Cohan, dated Jun. 24, 2009, an entire copy of which is incorporated herein by reference, further states: "Specifically, Boeing found that portions of the airframe—those where the top of the wings join the fuselage—experienced greater strain than computer models had predicted. Boeing could take months to fix the 787 design, run more ground tests and adjust computer models to better reflect reality." This article continues: "And this is what raises questions about the 787's safety. If engineers continue to be surprised by the 787's response to real-world operating stresses, there is some possibility that the testing process might not catch all the potential problems with the design and construction of the aircraft."

Significant problems have occurred in the past during the development of new airframes. For example, inadequate attention was paid the possibility of high stresses causing catastrophic metal fatigue during the development of the de Havilland Comet. High stresses were a surprise particularly around the square window corners. Such failure of adequate attention resulted in several notable crashes.

Another example is the explosive decompression in flight suffered by Aloha Airlines Flight 243. Water entering into an epoxy-aluminum bonded area caused the basic problem. Consequently, an epoxy resin failure between two laminated materials (in this case aluminum) has caused significant problems in the past.

SUMMARY OF THE INVENTION

An object of the invention is to provide methods and apparatus to use real-time measurement systems to detect the onset of compression induced micro-fracturing of fiber-reinforced composite materials.

Another object of the invention is to provide measurement means to detect the onset of compression induced micro-fracturing of fiber-reinforced composite materials to prevent catastrophic failures of aircraft components containing such materials.

Yet another object of the invention is to provide methods and apparatus to prevent fluids and gases from invading any compression induced microfractures through any coated surfaces of fiber-reinforced materials to reduce the probability of failure of such fiber-reinforced materials.

Another object of the invention is to provide a real time electronics system measurement means fabricated within a portion of an aircraft made of fiber-reinforced composite materials to detect the onset of compression induced micro-fracturing of the fiber-reinforced composite materials to prevent the catastrophic failure of the portion of the aircraft or portions of the aircraft proximate thereto.

Yet another object of the invention is to provide a real time electronics system measurement means to measure the differential resistivity of materials fabricated within a portion of an aircraft made of fiber-reinforced composite materials to detect the onset of compression induced micro-fracturing of the fiber-reinforced composite materials to prevent the catastrophic failure of the portion of the aircraft.

DESCRIPTION OF THE PREFERRED EMBODIMENTS

The fiber-reinforced wings and wing boxes of Boeing 787's are described very well in an article in The Seattle Times, dated Jul. 30, 2009, entitled "Double trouble for Boeing 787 wing" by Dominic Gates, that appears on the front page and on A8, an entire copy of which is incorporated herein by reference. That article provided several colored drawings showing the then existing wings and wing box assemblies, and the then proposed reinforcement of those assemblies.

Some aspects of FIGS. 1, 2, 3 and 4 herein are based on the information provided in that Jul. 30, 2009 article in The Seattle Times. Applicant is grateful for that information.

Figure 1:
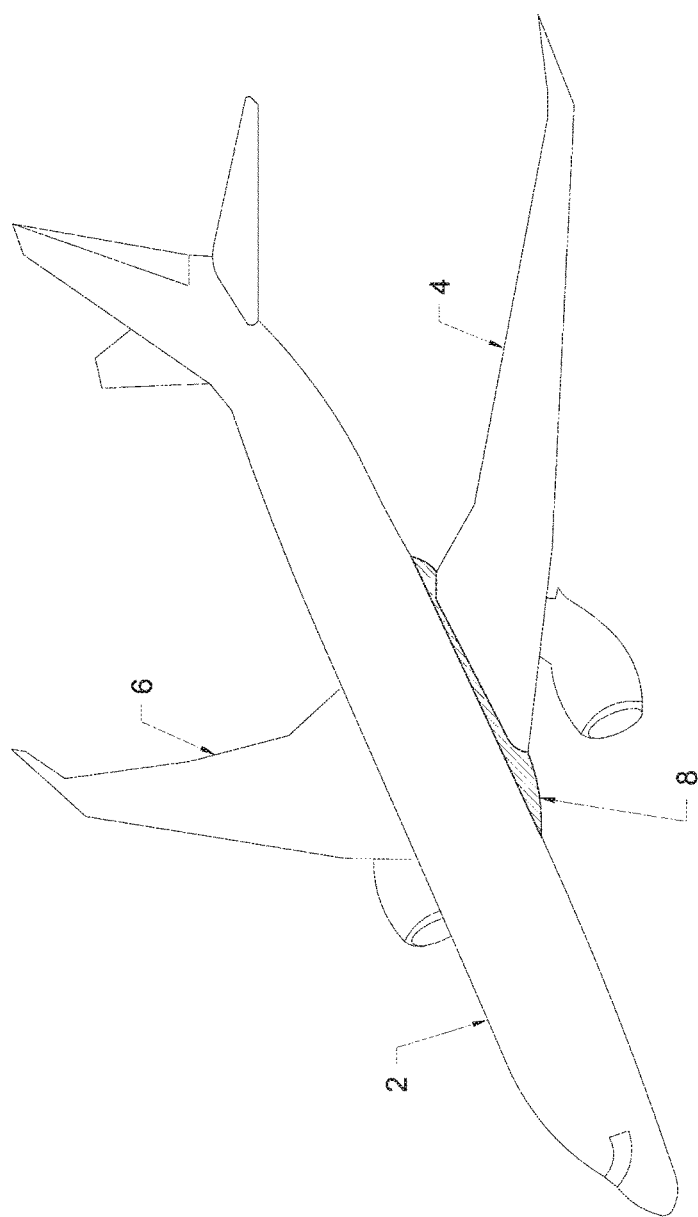
FIG. 1 shows an aircraft having substantial fiber-reinforced materials, such as a Boeing 787.

FIG. 1 shows an airplane 2 having substantial quantities of fiber-reinforced composite materials, that has a right wing 4 (when viewed standing in front of airplane 2), left wing 6, and center wing box 8. The wings and wing boxes are substantially fabricated from fiber-reinforced materials. In the Jul. 30, 2009 article, the airplane sketched was the Boeing 787. It should be appreciated that the inventions disclosed herein are not limited to the Boeing 787 nor to wings and wing boxes, but are applicable to any structure comprising fiber-reinforced materials.

Figure 2:
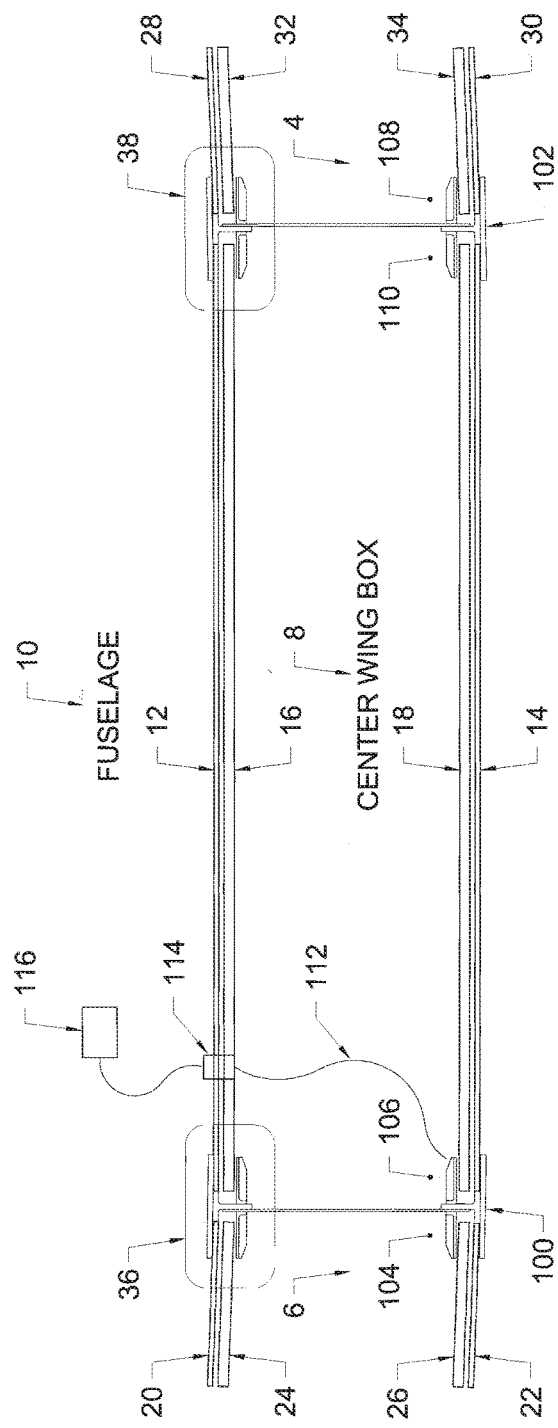
FIG. 2 shows an embodiment of how the right and left wings are attached to the center wing box, and an embodiment of the distribution of sensor array systems in a portion of the fiber-reinforced composite materials particularly subject to compressive stresses.

FIG. 2 shows a cross section view of the center wing box 8 in fuselage 10, having its top skin 12 and bottom skin 14, its top stringers 16, and its bottom stringers 18. Wing 6 has its top wing skin 20, bottom wing skin 22, its top stringers 24, and its bottom stringers 26. Wing 4 has its top wing skin 28, its bottom wing skin 30, its top stringers 32, and bottom stringers 34. Left wing connection apparatus 36 connects the left wing 6 to the mating portion of the center wing box. Upper right wing connection apparatus 38 connects the right wing 4 to the mating portion of the center wing box.

Figure 3:
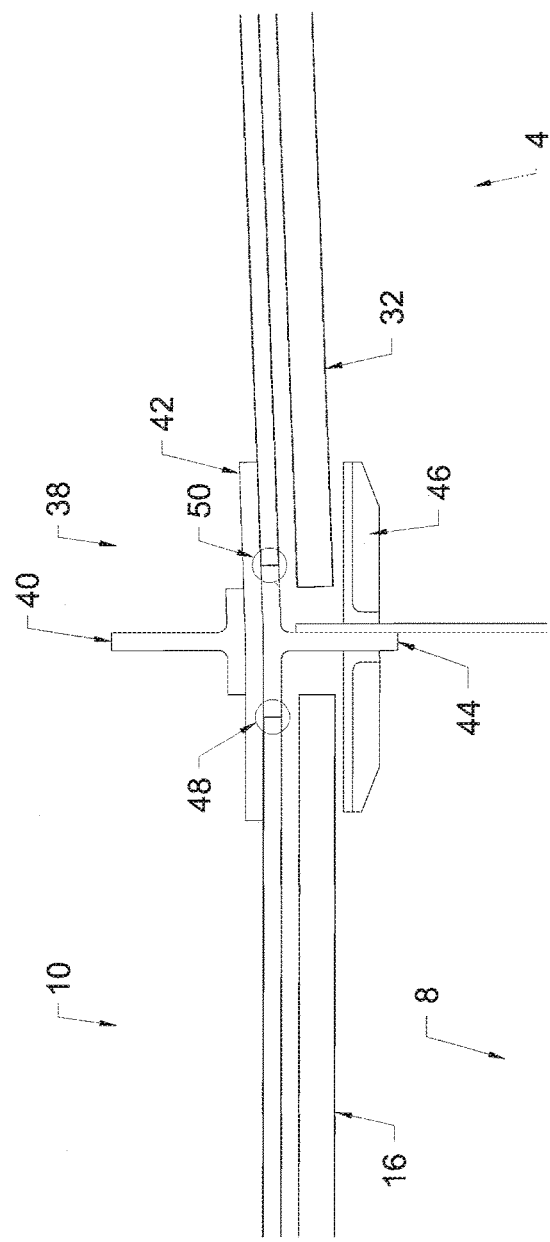
FIG. 3 shows the upper right wing connection apparatus of the embodiment of FIG. 2 which connects the upper right wing to the mating portion of the upper right center wing box.

FIG. 3 shows an expanded version of the upper right wing connection apparatus 38. Many of the various elements have already been identified above. In addition, the right-hand wall of the fuselage 40 is coupled to the center wing box 8 and to the right wing 4 by parts 42, 44, and 46. High stress points 48 and 50 were identified as being related to the failures of the wings and the center wing junction box during the tests described in the article dated Jul. 30, 2010.

Figure 4:
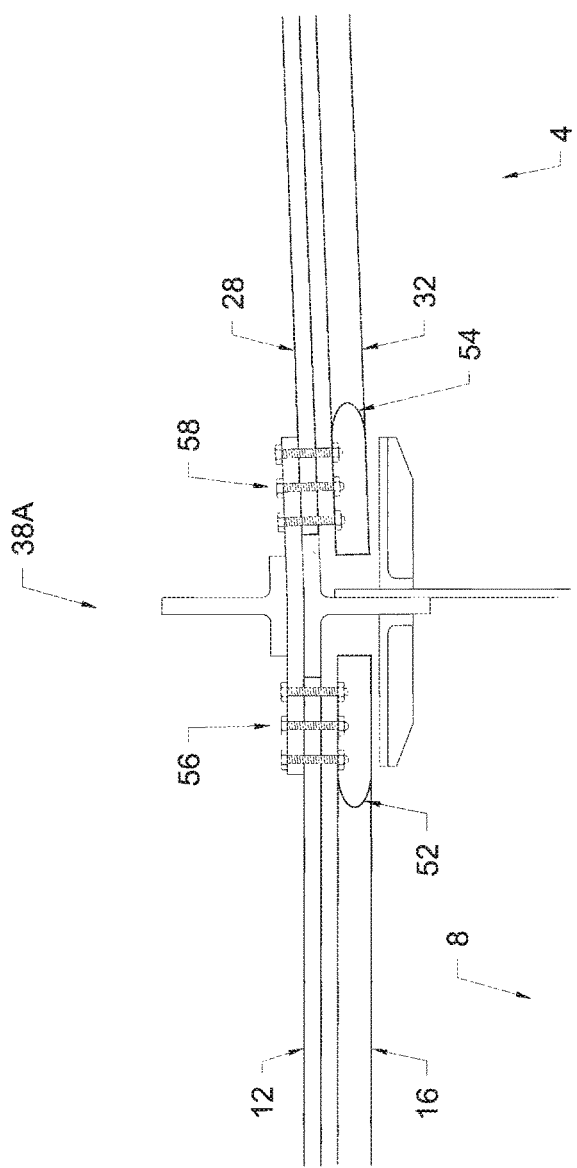
FIG. 4 shows modifications to the upper right wing connection apparatus of the embodiment of FIG. 2 which connects the upper right wing to the mating portion of the upper center wing box.

In FIG. 4, the modifications described in the article dated Jul. 30, 2010 are shown. U-shaped cutouts in the stringers 52 and 54 are shown, along with the addition of fastener bolts 56 and 58. Element 38A shows an expanded version of the upper right wing connection apparatus that has been modified.

Referring again to FIG. 2, lower left-wing connection apparatus 100 and lower right-wing connection apparatus 102 are areas which are in substantial compression. So, in these areas, the fiber-reinforced materials are in substantial compression. Consequently, sensor array systems 104, 106, 108, and 110 are shown as being placed in areas subject to substantial compressive forces applied to the fiber-reinforced composite materials. These sensor array systems are monitored to determine if microfractures are being produced, and to determine if fluids and gases are invading any such microfractures in the materials.

Information from the sensor arrays are sent via wires such as 112 through wing box to fuselage connector 114 to monitoring instrumentation 116. That monitoring instrumentation may be in the fuselage, or external to the fuselage, or may be connected by a wireless communications link. Power to any measurement devices in the sensor array systems are provided by wires such as 112. By "sensor array" is meant to include means to make a change to the materials (such as the conduction of electricity) and the measurement of a parameter (such as a change in resistance or resistivity of the materials).

To avoid fluid invasion problems, in several preferred embodiments, real-time measurement systems are described to detect the onset of compression induced micro-fracturing. So, not only would stress and strain be measured in live-time, but also whether or not fluids and gases have invaded the microfractures. In other preferred embodiments, the electrical resistivity between adjacent laminated sections is used as a convenient way to determine if there has been invasion of conductive fluids (such as salt water) into the microfractures. Extraordinarily precise differential measurements may be made of such resistivity, and the applicant has had many years of experience in such measurements during the development of the Through Casing Resistivity Tool. In other preferred embodiments, precise differential measurements are made in real-time of various dielectric properties that will allow the detection of non-conductive fluids and gases. In other embodiments, undue swelling of the composites are also directly measured with sensors that will give an advance indication of potential catastrophic failures due to fluid and/or gas invasion. In many embodiments, the sensors themselves are integrated directly into the composite materials during manufacture. In some embodiments, the existing carbon fibers already present may be used. Accordingly, there are many live-time measurements that we can use to prevent catastrophic failures.

Yet other embodiments of the invention provide inspection techniques based on measurements to determine invasion of fluids and gases into the composite materials is clearly needed.

A preferred embodiment of the invention describes a method to use real-time measurement systems to detect the onset of compression induced micro-fracturing of fiber-reinforced composite materials. In a preferred embodiment, the real-time measurement systems measure the electrical resistivity between different portions of the fiber-reinforced composite materials.

In selected embodiments, changes in time of electrical resistivity between different portions of the fiber-reinforced composite materials are used to determine the invasion of conductive fluids into the microfractures of the fiber-reinforced composite materials. In several preferred embodiments, fiber-reinforced composite materials comprise a portion of an umbilical in a subterranean wellbore that conducts electricity through insulated wires to an electric drilling machine. In other preferred embodiments, the fiber-reinforced composite materials comprise a portion of a Boeing 787 wing, 787 wing box assembly, and any combination thereof. The invention applies to fiber-reinforced composite materials used in any portion of an airplane.

In other preferred embodiments, the real-time measurement systems measure dielectric properties between different portions of fiber-reinforced composite materials.

In selected embodiments, changes in time of measured dielectric properties between different portions of the fiber-reinforced composite materials are used to determine the invasion of fluids and gases into the microfractures of said fiber-reinforced composite materials. In selected preferred embodiments, these methods are used to monitor fiber-reinforced composite materials that comprise a portion of an umbilical in a subterranean wellbore. In other selected embodiments, the methods and apparatus are used to monitor fiber-reinforced composite materials comprise a portion of a Boeing 787 wing, 787 wing box assembly, and any combination thereof, or any other portion of fiber-reinforced composite materials comprising any portion of an airplane.

Selected preferred embodiments of the invention provide methods and apparatus wherein substantial portions of the real-time measurement systems are fabricated within the fiber-reinforced composite materials. In selected preferred embodiments, changes in time of measured properties are used to determine the invasion of fluids and gases into the microfractures of the fiber-reinforced composite materials.

In selected embodiments, measurement means are provided to detect the onset of compression induced microfracturing of fiber-reinforced composite materials to prevent catastrophic failures of aircraft components containing such materials.

In other preferred embodiments, the measurement means further includes means to detect and measure the volume of fluids and gases that have invaded the microfractures in the fiber-reinforced composite materials.

In yet another preferred embodiment, methods and apparatus are provided to prevent fluids and gases from invading any compression induced microfractures of fiber-reinforced materials to reduce the probability of failure of such materials. Such methods and apparatus include special coating materials that coat fabricated fiber-reinforced materials, wherein such special materials are defined to be a coating material means. Such methods and apparatus further includes a coating material means is used to coat fiber-reinforced composite materials in visually inaccessible areas of airplanes. Such methods and apparatus further include special materials incorporated within the fiber-reinforced materials that are hydrophilic (tend to repel water). Such methods and apparatus further include special materials incorporated within the fiber-reinforced materials that absorb during a chemical reaction that produces a new portion of the matrix material in the fiber-reinforced composite material. Such methods and apparatus further includes special materials incorporated within the fiber-reinforced materials that absorb gases. Such methods and apparatus yet further includes self-healing substances designed to fill any such microfractures in the fiber-reinforced materials. Such methods and apparatus yet further include self-healing substances whereby at least one component of the matrix material used to make the fiber-reinforced composite material. Such matrix material may be comprised of at least an epoxy resin material and a hardener component. The self-healing substance may further include a hardener component designed to set-up slowly over a period in excess of one year.

Another preferred embodiment of the invention includes methods and apparatus wherein predetermined compressional stresses induce a chemical reaction within a special material fabricated within the fiber-reinforced composite material that prevents fluids and gases from invading any compression induced microfractures of fiber-reinforced materials to reduce the probability of failure of such materials. In several preferred embodiments, such predetermined compressional stresses induce a structural phase transition within a special material fabricated within the fiber-reinforced composite material that prevents fluids and gases from invading any compression induced microfractures of fiber-reinforced materials to reduce the probability of failure of such materials.

Further embodiments include methods and apparatus wherein at least a portion of the fiber-reinforced composite material is exposed to a relatively high-pressure inert gas which slowly diffuses through other portions of the fiber-reinforced composite material to prevent other fluids and gases from invading any compression induced microfractures of the fiber-reinforced material to reduce the probability of failure of the material. The inert gas can include dry nitrogen. Such methods and apparatus apply to any portion of a fiber-reinforced material that is comprised of at least one channel within said fiber-reinforce composite material.

Yet other preferred embodiments provide additional special fibers that are added during the manufacturing process of a standard fiber-reinforced composite material to make a new special fiber-reinforced material to prevent fluids and gases from invading any compression induced microfractures of said special fiber-reinforced material to reduce the probability of failure of said special fiber-reinforced material. Such special fibers include fibers comprised of titanium. Such special fibers include fibers comprised of any alloy containing titanium.

Other embodiments provide special fibers that are added during the manufacturing process of a standard fiber-reinforced composite material to make a new special fiber-reinforced material to reduce the probability of the formation of stress-induced microfractures in said material. Such special fibers include fibers comprised of titanium. Such special fibers include fibers comprised of any alloy containing titanium.

Other preferred embodiments provide methods and apparatus to isolate the wing boxes of composite aircraft from environmental liquids, such as water, and from environmental gases, such as jet exhaust to reduce the probability of failure of such materials. Such methods and apparatus include means to prevent fluids and gases from invading any compression induced microfractures through any coated surfaces of fiber-reinforced materials to reduce the probability of failure of such fiber-reinforced materials.

Other selected embodiments of the invention incorporate the relevant different types of physical measurements defined in U.S. Provisional Patent Application 61/270,709, filed Jul. 9, 2010, an entire copy of which is incorporated herein by reference. For example, such physical measurements include acoustic transmitters and receivers, ultrasonic transmitters and receivers, phased array ultrasonics, thermosonics, air coupled ultrasonics, acoustic resonance techniques, x-ray techniques, radiography, thermal wave imaging, thermography and shearography. These cited physical measurements, and selected additional physical measurements described in the References incorporated into this document, may be used to make the basic sensors of a real time electronics system measurement means fabricated within a portion of an aircraft made of fiber-reinforced composite materials to detect the onset of compression induced micro-fracturing of said fiber-reinforced composite materials to prevent the catastrophic failure of said portion of said aircraft.

Reference is made to the article entitled "Nondestructive Inspection of Composite Structures: Methods and Practice" by David K. Hsu, 17th World Conference on Nondestructive Testing, 25-28 Oct. 2008, Shanghai, China, an entire copy of which is incorporated herein by reference. This is a review article of methods and apparatus to inspect composite materials and will be hereinafter abbreviated as Hsu, 2008.

Many non-destructive tests are reviewed, which include water- and air-coupled ultrasound bond testing, manual and automated tap testing, thermography, and shearography (hereinafter collectively, "standard techniques").

In the case of one of the mechanisms described herein, composite materials under compression in or near the wing box ingest or soak-up water, jet fuel, etc. and are subject to a catastrophic delimitation.

The interior portion of the wing box is very hard to access. Some portions subject to testing are deep into the wing, significant distances from the outer skin of the aircraft. The interior portion of the wing box is not subject to any external visual inspection from outside the aircraft. Nor will any of the "standard techniques" noted above work to determine the failure mechanism described herein on an interior portion of the wing box from outside the aircraft.

An individual can access some areas of the interior portion of the wing box from inside the wing. There are crawl spaces. Some hand-held inspection tools, such as a hand-held tap tester, or hand-held acoustic device, could be used by an individual to inspect certain portions of the interior portion of the wing box. But, the sensitivity of these are severely limited.

In Section 4.3 of Hsu, 2008, the article talks about sensitivities . . . "as small as 3 mm (⅛") diameter can be detected . . . ". This is a pretty large hole and not sensitive enough to determine the presence or absence of microfractures of the type produced by the mechanism described herein.

In addition, reference is made to an article in USA Today, entitled "Signs of pre-existing fatigue found on Southwest aircraft", by Roger Yu, Apr. 4, 2011 (the "USA Today Article"), an entire copy of which is incorporated herein by reference. The USA Today Article states in part:

"The FAA said it no longer believes airplanes can fly forever," Goldfarb said. "They have life limits. And because of extensive fatigue, airlines need to retire them at a limit. (The FAA) thinks just (having) inspection is not enough. These cracks can propagate quickly.

The USA Today Article further states in part:

In justifying the new rules, the FAA said, "Existing inspection methods do not reliably detect widespread fatigue damage because cracks are initially so small and may then link up and grow so rapidly that the affected structure fails before an inspection can be performed to detect the cracks."

So, even after many years of flying, and after much study, the FAA concludes that they do not have a good way to determine what is going to happen on a given aircraft by using present inspection techniques. Please note the first above quote from the USA Today Article implies that cracks are to be expected. Furthermore, microcracks are apparently common in aluminum—which are, by analogy, just the type of microcracks in composites that can result in the failure mechanism described herein.

In the second above quote from the USA Today Article, microcracks may link up and grow very rapidly, a phenomenon which might be called "swarming of microcracks" for the purposes herein. If such swarming occurs, and fluids such as water, jet fuel, etc. invade the structure, the composite can catastrophically fail within a short period of time. This is one mechanism described herein.

None of the "standard techniques" noted above are adequate to monitor the failure mechanism described herein. However, resistivity measurements are cited herein as having the resolution to detect and monitor this problem.

Figure 5:
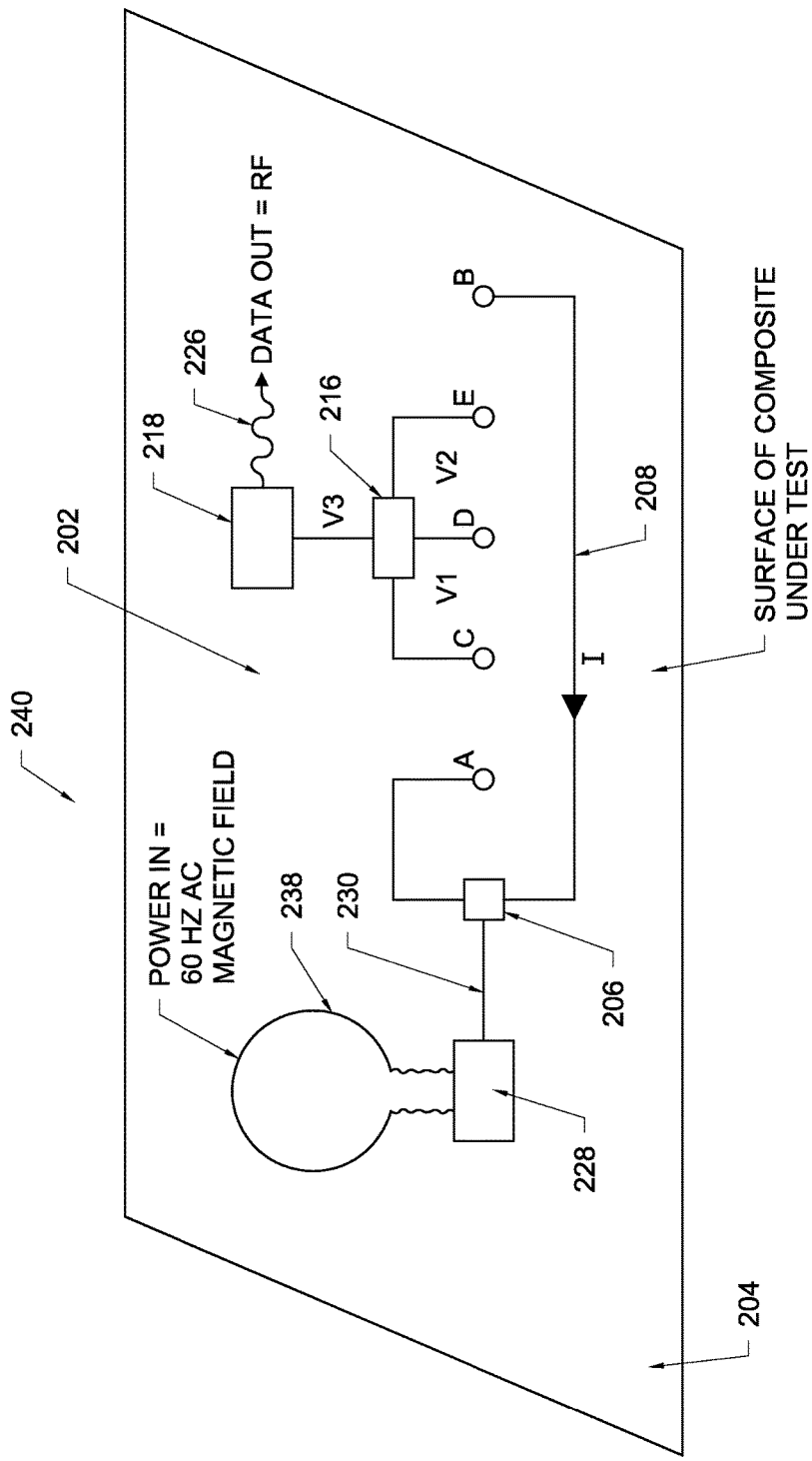
FIG. 5 shows one embodiment of a real time electronics system measurement means fabricated within a portion of an aircraft made of fiber-reinforced composite materials to detect the onset of compression induced micro-fracturing.

Accordingly, another preferred embodiment of the invention is shown in FIG. 5. That FIG. 5 shows a Differential Form of a Four Point Resistivity Measurement generally identified with numeral 202. This type of measurement is particularly sensitive and immune to electromagnetic interference. Some engineers also call it a Four Point Resistance Measurement provided the physical dimensions are defined to turn the resistance measured into resistivity. The measurement is being performed on a material 204 that is a fiber-reinforced composite material such as that found in a wing or wing box of a Boeing 787. Such a fiber-reinforced material also includes materials identified as a carbon fiber-reinforced polymer material of the type used in an Airbus A350 wing or wing box. The material 204 has a surface that is defined as "SURFACE OF COMPOSITE UNDER TEST", which legend is defined in FIG. 5.

In FIG. 5, electrical current generation means 206 is used to generate electrical current identified with the legend I in FIG. 5. That electrical current I is passed between current conducting electrode A and current conducting electrode B through material 204, legends further identified on FIG. 5. The current conducting circuit shown is completed with insulated wire 208.

In FIG. 5, voltage measurement electrodes C, D, and E are in electrical contact with material 204, which legends are defined in FIG. 5. Current passing between current conducting electrodes A and B will generate a voltage difference V1 between voltage measurement electrodes C and D, which legend V1 is defined in FIG. 5. Current passing between current conducting electrodes A and B will also generate a voltage difference V2 between voltage measurement electrodes D and E, which legend V2 is defined in FIG. 5.

The voltages V1 and V2 are provided to the respective inputs 210, 212, and 214 of processing electronics 216. The inputs are not shown in FIG. 5 for clarity, but would be understood by those of skill in the art. Processing electronics 216 provides detection, amplification, logical processing, and other electronics to provide an output voltage V3, a legend identified in FIG. 5. The output voltage V3 is given by the following:

$$V3 = S1 \cdot K1 \cdot (R2 - R1) \qquad \text{Equation 1.}$$

In Equation 1, K1 is a proportionality constant that converts resistance to resistivity units appropriate for the geometry of the various defined electrodes in electrical contact with material 204. It should be noted that resistance is normally measured in ohms, and resistivity has the units of ohm-meters. The parameter S1 is an amplification factor sometimes helpful to overcome environmental noise.

Voltage V3 is proportional to the difference in resistance between R2 and R1. The difference in resistance can be measured to many decimal points—six is typical. The inventor has previously done such measurements to an accuracy of eleven decimal places.

The voltage V3 is provided to an input of communications electronics module 218. The input 220 of communications module 218 and the insulated wire 222 carrying voltage V3 are not shown in FIG. 5 for the purposes of clarity but would be understood by those of skill in the art.

In the particular embodiment of the invention shown in FIG. 5, communications module 218 provides the data including V3 to a remote Receiver Unit (224—not shown in FIG. 5) but understood by those of skill in the art. The communication module 218 provides the data via radio frequency communications 226 that is further identified with legend "DATA OUT=RF" in FIG. 5.

Power supply 228 provides electrical power to electrical current generation means 206 via insulated wire 230. Power supply 228 also provides electrical power to processing module 216 via insulated wire 232 (numeral not shown in FIG. 5). Power supply 228 also provides electrical power to communications module 218 via insulated wire 233 (numeral not shown in FIG. 5).

In this particular preferred embodiment of the invention, power supply 228 obtains its power from an AC magnetic field identified by the legend "POWER IN=60 HZ AC MAGNETIC FIELD" in FIG. 5. In one embodiment, the AC Magnetic Field is provided by a remote Power Transmitter Unit 236 (which numeral is not shown in FIG. 5 but would be understood by a person of ordinary skill in the art). The AC Magnetic field generated by remote Power Transmitter Unit 236 is intercepted by insulated coil of wire 238. The changing AC Magnetic Field induces a voltage in the insulated coil of wire 238 and is used to provide electrical power to power supply 228. In several embodiments of the invention, a battery is included within power supply 228 to store energy received from the remote Power Transmitter Unit 236 that in turn may be used to power elements 206, 216 and 226 in FIG. 5 when the Power Transmitter Unit is not nearby (such as during flight of an aircraft).

The electronic elements, including the current conducting electrodes, the voltage measurement electrodes, elements 206, 216, 218, 228, 230, 238, any electrical conductors required, the remote Power Transmitter Unit 236, and remote Receiver Unit 224 are defined for the purposes herein as a real time electronics measurement system means 240 to provide Differential Four Point Resistivity Measurements of the material 204 under test. The various components of the electronics means 240 may be incorporated within the body of the material 204, or on a surface of the material —identified by the legend previously described, or any combination thereof in various embodiments.

As stated before, the electrical current generation means 206 generates the electrical current identified with the legend I in FIG. 5. The electrical current I may be chosen to be DC, AC, DC plus AC, or may have an arbitrary function in time. There are advantages to each choice. Depending on the choice, the resulting voltages V1, V2, and V3 will be DC, AC, DC plus AC, or may have an arbitrary function in time.

DC current may be the simplest to implement, but may be subject to adverse noise problems. AC is a good choice, and phase sensitive detection methods may be used to enhance the signal and reduce the effect of any noise present. (For example, see Section 15.15 entitled "Lock-in detection" in the book entitled "The Art of Electronics" by Horowitz and Winfield identified in the References hereto.) The DC plus AC has some advantages of both. If the current is chosen to have an arbitrary function in time, signal averaging or "signal stacking" techniques may be used to enhance the signal and reduce the noise. (For example, see Section 15.13 entitled "Signal averaging and multichannel averaging" in the book entitled "The Art of Electronics" previously mentioned in this paragraph.)

In a particularly simple approach, the voltage from just one pair V1 can be measured to extract some information especially if combined with phase sensitive detection methods and or signal averaging methods as appropriate.

Figure 6:
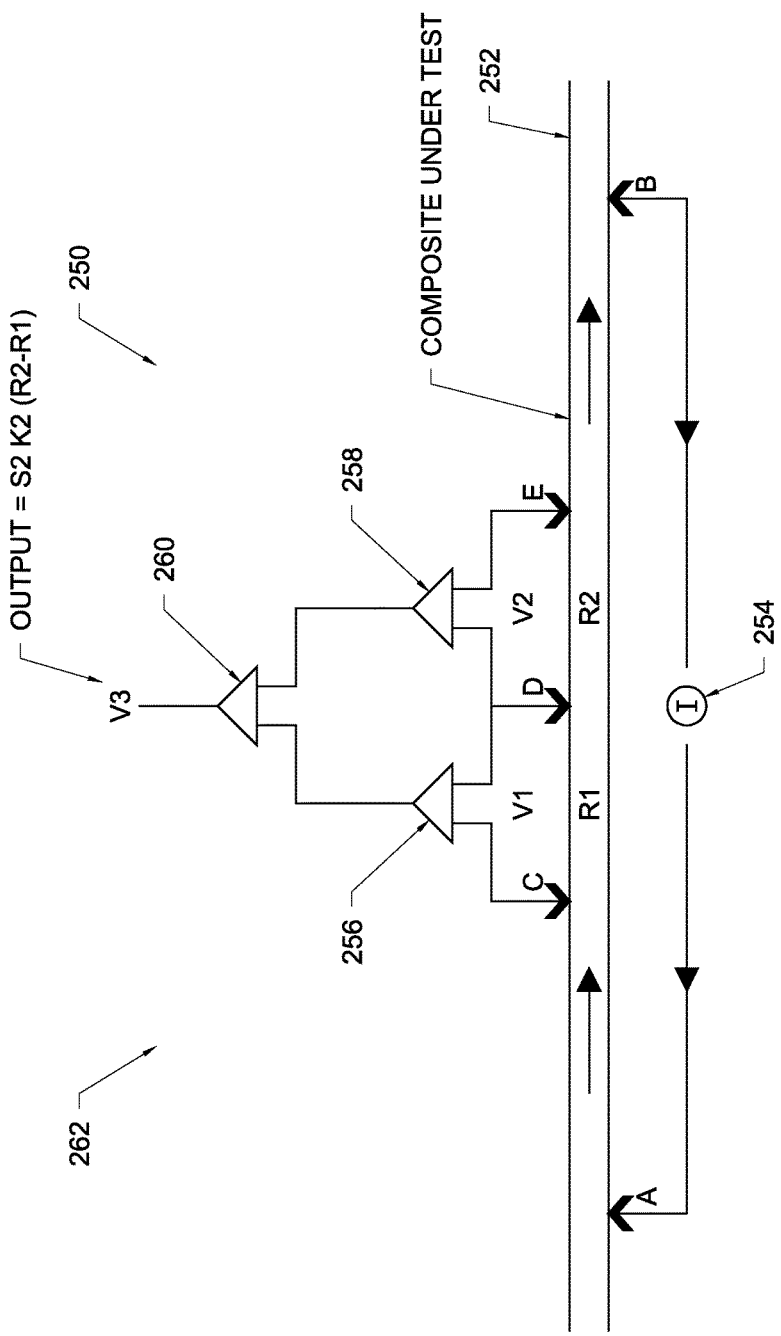
FIG. 6 shows one embodiment of a real time electronics system measurement means particularly suited for a laboratory demonstration of the measurement principles applied in the embodiment shown in FIG. 5.

FIG. 6 shows an experimental arrangement 250 perhaps most suited in a laboratory environment to convey the principles related to the above defined measurement apparatus. A particular sample 252 is a COMPOSITE UNDER TEST, a legend defined in FIG. 6. The current supply 254 provides current I to current conducting electrodes A and B. Voltage measurement electrodes C, D, and E are in electrical contact with the COMPOSITE UNDER TEST 252. Differential amplifiers 256, 258, and 260 provide output voltage V3. In this case, the output voltage V3 is given by:

$$V3 = S2 \cdot K2 \cdot (R2 - R1) \quad \text{Equation 2.}$$

In Equation 2, S2 is the appropriate proportionality constant that converts resistance to resistivity units, and S2 is the appropriate overall amplification of the system. FIG. 6 shows a laboratory version of a real time electronics system measurement means 262 to provide Differential Four Point Resistivity Measurements of the material 204 under test. Similar comments made in relation to FIG. 5 for using DC, AC, DC plus AC, and arbitrary waveforms also apply to the current I in FIG. 6.

It is appropriate to return again to FIG. 5. In one embodiment, the apparatus shown in FIG. 5 is a monolithic assembly in contact with the composite. In another embodiment, it is sealed against the surface of the composite under test. In yet another embodiment, it is simply epoxied in place. In another embodiment, an inspector applying a magnetic field from outside the skin of the aircraft, will prompt the device to measure V3 and those results are sent to a receiver box on the exterior of the aircraft (not shown). In another embodiment, the results are sent to a receiver box on the interior of the aircraft (not shown). In various different embodiments, the results can be sent to any selected location (not shown). Furthermore, from such a selected location, the results can be further relayed to other specific locations by suitable communications systems (not shown) as would be appreciated by those of skill in the art upon reading this disclosure.

So, the apparatus can be retrofitted onto a wing box of a 787 by a worker crawling through the crawl space. No extra wires are used to power the apparatus. The apparatus in FIG. 5 does have the sensitivity to detect changes in the microfractures within the composite and the presence of fluids such as water or jet fuel. Such monitoring can be used to prevent the catastrophic failure of composites within the wing box region of the 787. Similar comments apply to other composite structures within the 787 or other aircraft having composite structures such as the Airbus 350.

In yet other embodiments of the invention, it is not necessary to have the solenoid powered—battery combination. Rather, in analogy with some old-time wrist watches that needed no winding, a motion powered generator can be made a part of the apparatus shown in FIG. 5. For example, a small round magnet rolling around in a cavity surrounded with pick-up coils can be used to generate power and charge the battery.

Different embodiments of the apparatus in FIG. 5 can perform and store its measurements periodically. After the plane has landed, a hand-held Reader outside the aircraft can then send an RF signal to a receiver coil in the device to "Start Read". The RF transmitter can then send RF to the hand-held Reader that receives the data. The hand-held Reader can then be connected wirelessly to a remote computer. The Reader in this paragraph is another embodiment of the Receiver Unit described above.

In another embodiment of the invention, the apparatus shown in FIG. 5 is provided with cell phone-like receiver and transmitter capabilities. After the plane is parked, a call from an external computer to the on-board "cell phone" is used to "Start Read". Then, data is communicated to the computer that made the call—using tone's for digits in one embodiment. Tones will work here in one embodiment because not much data is involved in particularly simple embodiments of the invention.

In yet another embodiment of the invention, and if the aircraft itself supports cell phone calls at any location world-wide, then the aircraft supported cell phone network can be used to "Start Read" and to download the data seamlessly, anywhere in the world, all the time, any time. With such a network, the apparatus in FIG. 5 can be programmed to "wake up" and send an alarm if the data shows there is a problem.

In yet other embodiments of the invention, similar comments apply to Wi-Fi networks or any other communication networks which aircraft support now and into the future.

For example, one preferred embodiment the following steps are executed:

a. select a portion of the wing box for monitoring;

b. epoxy the measurement apparatus to the portion of the wing box;

c. when the plane lands, the results will be automatically sent by auto-dialing to a cell phone number.

In yet other embodiments, the electrical power and the communications to the measurement apparatus may be made by conventional wiring to aircraft wiring bus. In such case, methods and apparatus defined in U.S. Provisional Patent Application Ser. No. 61/849,585, filed on Jan. 29, 2013 (PPA-101), and in U.S. Provisional Patent Application Ser. No. 61/850,095, filed on Feb. 9, 2013 (PPA-102), and in U.S. Provisional Patent Application Ser. No. 61/850,774, filed on Feb. 22, 2013 (PPA-103) may be used to minimize undesirable effects of Groundloops on the measurement apparatus. Entire copies of these three U.S. Provisional Patent Applications have been previously incorporated in their entirety herein by reference.

REFERENCES

Patent Literature

The following patents and published patent applications are related to fiber, reinforced and/or composite materials relevant to aircraft. Each is incorporated herein in its entirety by reference.

U.S. Pat. No. 6,379,762 entitled "Composite Structure of Expandable Matrix and a Reinforcing Medium" filed 2000 Mar. 7;

U.S. Pat. No. 5,955,387 entitled "Microform Composite With Intermediate Reinforcing Fiber Cloth" filed 1997 Jun. 23;

U.S. Pat. No. 5,944,060 entitled "Composite Duct System" filed 1995 Dec. 26;

U.S. Pat. No. 5,705,796 entitled "Reinforced Composites Formed Using Induction Thermoplastic Welding" filed 1996 Feb. 28;

U.S. Pat. No. 5,378,109 entitled "Co-Cured Composite Fan Blade and Method" filed 1991 Aug. 28;

U.S. Pat. No. 4,966,802 entitled "Composites Made of Fiber Reinforced Resin Elements Joined by Adhesive" filed 1989 May 16;

U.S. Pat. No. 4,789,416 entitled "Method of Manufacturing a Preform from Fiber Reinforced Composite Material" filed 1983 Jan. 19;

U.S. Pat. No. 4,786,343 entitled "Method of Making Delamination Resistant Composites" filed 1985 May 10;

U.S. Pat. No. 4,752,537 entitled "Metal Matrix Composite Fiber Reinforced Weld" filed 1986 Apr. 21;

U.S. Pat. No. 4,625,095 entitled "Method of Welding Metal Matrix Composites" filed 1985 Jun. 10;

U.S. Pat. No. 4,571,355 entitled "Fiber Reinforced Resin Composites Formed of Basic Ply Blankets" filed 1984 Nov. 28;

U.S. Pat. No. 4,567,076 entitled "Composite Material Structure with Integrated Insulating Blanket and Method of Manufacture" filed 1984 Mar. 23;

U.S. Pat. No. 4,395,450 entitled "Composite Structural Skin Spar Joint and Method of Making" filed 1981 Sep. 30;

U.S. Pat. No. 4,331,723 entitled "Advanced Composite" filed 1980 Nov. 5;

U.S. Pat. No. 4,198,018 entitled "Blended Wing-Fuselage Frame Made of Fiber Reinforced Resin Composites" filed 1978 Mar. 13;

U.S. Pat. No. 8,043,554 entitled "Manufacturing Process Using Bladderless Mold Line Conformal Hat Stringer" filed 2007 Jun. 8;

U.S. Pat. No. 7,807,249 entitled "Composite Article Having Reinforcing Fibers Oriented to Suppress or Delay Ply Splitting" filed 2008 Dec. 19;

U.S. Pat. No. 7,371,451 entitled "Sandwich Type Construction Structural Panel Having Foam Tube Core" filed 2002 Aug. 6;

U.S. Pat. No. 6,595,751 entitled "Composite Rotor Having Recessed Radial Splines for High Torque Application" filed 2000 Jun. 8;

U.S. Pat. No. 6,136,237 entitled "Method of Fabricating a Fiber-Reinforced Ceramic Matrix Composite Part" filed 1999 Apr. 13;

U.S. Pat. No. 5,975,237 entitled "Reinforcing Structure for Engine Nacelle Acoustic Panel" filed 1998 Feb. 19;

U.S. Pat. No. 5,817,738 entitled "Conductive, Multidimensional Oligomers and Blends" filed 1988 Jun. 27;

U.S. Pat. No. 5,753,570 entitled "Reinforced Ceramic Microform Composite" filed 1995 Jun. 5;

U.S. Pat. No. 5,286,811 entitled "Blended Polyimide Oligomers and Method of Curing Polyimides" filed 1992 May 21;

U.S. Pat. No. 5,198,282 entitled "Tandem Ceramic Composite" filed 1987 Oct. 8;

U.S. Pat. No. 4,876,328 entitled "Polyamide Composition" filed 1987 Jun. 12;

U.S. Pat. No. 4,741,943 entitled "Aerodynamic Structures of Composite Construction" filed 1985 Dec. 30;

U.S. Pat. No. 4,683,368 entitled "Weld Rod" filed 1986 Apr. 21;

U.S. Pat. No. 8,430,759 entitled "Joint for Composite Tube" filed 2012 Mar. 22;

U.S. Pat. No. 8,163,368 entitled "Composite Leg for Landing Gear Assembly" filed 2008 Dec. 22;

U.S. Pat. No. 8,132,430 entitled "Glass Fibers Having Improved Strength" filed 2011 Jun. 2;

U.S. Pat. No. 7,387,277 entitled "Aircraft Wing Composed of Composite and Metal Panels" filed 2004 Dec. 29;

U.S. Pat. No. 6,114,050 entitled "Titanium-Polymer Hybrid Laminates" filed 1998 Dec. 29;

U.S. Pat. No. 6,027,798 entitled "Pin-Reinforced Sandwich Structure" filed 1996 Jan. 3;

U.S. Pat. No. 5,980,665 entitled "Z-pin Reinforced Bonds for Connecting Composite Structures" filed 1996 May 31;

U.S. Pat. No. 5,972,524 entitled "Double Lap Joint with Welded Z-Pins" filed 1997 Oct. 14;

U.S. Pat. No. 5,935,698 entitled "Composites Joined with Precured, Z-Pinned Strips" filed 1997 Mar. 7;

U.S. Pat. No. 5,935,680 entitled "Interlaced Z-Pin Sandwich Structure" filed 1997 Aug. 22;

U.S. Pat. No. 5,115,087 entitled "Coreactive Imido Oligomer Blends" filed 1988 Mar. 29;

U.S. Pat. No. 4,900,383 entitled "Convolutely Lined and Wrapped Composite Tubes" filed 1988 Apr. 19;

U.S. Pat. No. 4,755,904 entitled "Lightning Protection System for Conductive Composite Material Structure" filed 1986 Jun. 6;

U.S. Pat. No. 4,636,422 entitled "Composite Fiber Reinforced Molded Structure for Dimple Control" filed 1985 Jul. 26;

U.S. Pat. No. 4,565,595 entitled "Method of Making Composite Aircraft Wing" filed 1983 Jun. 6;

U.S. Pat. No. 4,556,591 entitled "Conductive Bonded/Bolted Joint Seals for Composite Aircraft" filed 1981 Sep. 25;

U.S. Pat. No. 8,419,876 entitled "Flame Retardant Composite Structures and Method of Making the Same" filed 2009 Sep. 22;

U.S. Pat. No. 8,383,028 entitled "Method of Manufacturing Co-Molded Inserts" filed 2008 Nov. 13;

U.S. Pat. No. 8,297,555 entitled "Systems and Methods for Reducing Noise in Aircraft Fuselages and Other Structures" filed 2011 Oct. 24;

U.S. Pat. No. 8,141,393 entitled "Glass Fibers Having Improved Durability" filed 2011 Jun. 2;

U.S. Pat. No. 8,097,106 entitled "Method for Fabricating Composite Structures Having Reinforced Edge Bonded Joints" filed 2007 Jun. 28;

U.S. Pat. No. 8,052,826 entitled "Method of Making Bead-Stiffened Composite Parts and Parts Made Thereby" filed 2009 Mar. 24;

U.S. Pat. No. 8,042,768 entitled "Systems and Methods for Reducing Noise in Aircraft Fuselages and Other Structures" filed 2010 Aug. 5;

U.S. Pat. No. 7,837,147 entitled "Systems and Methods for Reducing Noise in Aircraft Fuselages and Other Structures" filed 2005 Mar. 18;

U.S. Pat. No. 7,755,351 entitled "Method and Apparatus for Detecting Inconsistencies in Fiber Reinforced Resin Parts Using Eddy Currents" filed 2007 Jan. 23;

U.S. Pat. No. 7,721,495 entitled "Composite Structural Members and Methods for Forming the Same" filed 2005 Mar. 31;

U.S. Pat. No. 7,561,402 entitled "Gap Lightning Surface Protection of Composite Structures" filed 2006 Feb. 24;

U.S. Pat. No. 7,357,014 entitled "Porosity Reference Standard Utilizing One or More Discrete Wires" filed 2005 Nov. 29;

U.S. Pat. No. 6,758,386 entitled "Method of Joining Ceramic Matrix Composites and Metals" filed 2001 Sep. 18;

U.S. Pat. No. 6,719,870 entitled "Fastenerless Internal Support for Hollow Structures" filed 2000 Dec. 15;

U.S. Pat. No. 6,544,366 entitled "Composite Member Having Increased Resistance to Delamination and Method of Making Same" filed 2001 Jul. 5;

U.S. Pat. No. 6,277,463 entitled "Composite Member Having Increased Resistance to Delamination and Method of Making Same" filed 1998 Aug. 28;

U.S. Pat. No. 6,122,884 entitled "Selective Metal Matrix Composite Reinforcement by Laser Deposition" filed 2000 Jan. 11;

U.S. Pat. No. 6,074,716 entitled "Weavable Metal Matrix Impregnated Tow Composite Material" filed 1997 Jun. 10;

U.S. Pat. No. 6,064,031 entitled "Selective Metal Matrix Composite Reinforcement by Laser Deposition" filed 1998 Mar. 20;

U.S. Pat. No. 6,051,302 entitled "Thrust Reverser Inner Wall" filed 1997 Aug. 1;

U.S. Pat. No. 6,029,269 entitled "Ballistic-Resistant Helmet and Method for Producing the Same" filed 1997 Dec. 22;

U.S. Pat. No. 5,916,469 entitled "Susceptor Integration into Reinforced Thermoplastic Composites" filed 1996 Jul. 29;

U.S. Pat. No. 5,866,272 entitled "Titanium-Polymer Hybrid Laminates" filed 1996 Jan. 11;

U.S. Pat. No. 5,829,716 entitled "Welded Aerospace Structure Using a Hybrid Metal Webbed Composite Beam" filed 1995 Jun. 7;

U.S. Pat. No. 5,736,222 entitled "Interlaced Z-Pin Structures" filed 1996 Mar. 19;

U.S. Pat. No. 5,723,849 entitled "Reinforced Susceptor for Induction or Resistance Welding of Thermoplastic Composites" filed 1995 Jun. 6;

U.S. Pat. No. 5,705,795 entitled "Gap Filling for Thermoplastic Welds" filed 1995 Jun. 6;

U.S. Pat. No. 5,686,038 entitled "Resin Transfer Molding of Composite Materials that Emit Volatiles during Processing" filed 1995 Jun. 6;

U.S. Pat. No. 5,645,925 entitled "Advanced Composite Blends" filed 1990 Nov. 29;

U.S. Pat. No. 5,569,343 entitled "Ceramic Fabric Reinforced Fiber/Microparticle Ceramic Composite" filed 1990 Jun. 13;

U.S. Pat. No. 5,425,973 entitled "Integral Overwrap Shield" filed 1985 Dec. 27;

U.S. Pat. No. 5,368,807 entitled "Method for Vacuum Bag Molding Fiber Reinforced Resin Matrix Composites" filed 1990 Dec. 3;

U.S. Pat. No. 5,345,397 entitled "Optimal Composite Curing System and Method" filed 1991 Nov. 25;

U.S. Pat. No. 5,248,242 entitled "Aerodynamic Rotor Blade of Composite Material Fabricated in One Cure Cycle" filed 1990 Sep. 28;

U.S. Pat. No. 5,085,921 entitled "Decorative Laminates with Heat Release Reducing and Ink Discoloration Preventive Protective Layer" filed 1989 Dec. 27;

U.S. Pat. No. 5,077,106 entitled "Convolutely Lined and Wrapped Composite Tubes" filed 1989 Oct. 3;

U.S. Pat. No. 5,066,541 entitled "Heterocycle Oligomer Blends" filed 1988 Dec. 16;

U.S. Pat. No. 4,883,971 entitled "Method and Apparatus for Determining Infrared Signature of Objects" filed 1988 Dec. 19;

U.S. Pat. No. 4,851,501 entitled "Polyethersulfone Prepregs, Composites, and Blends" filed 1987 Dec. 17;

U.S. Pat. No. 4,720,255 entitled "Apparatus for Planar Forming of Zero Degree Composite Tape" filed 1986 Jul. 7;

U.S. Pat. No. 4,655,417 entitled "Molded Ejection Seat Having an Integrated Rocket Motor Assembly" filed 1984 Sep. 28;

U.S. Pat. No. 4,615,935 entitled "Glass Fiber Reinforced Ceramic Preform and Method of Casting It" filed 1985 Apr. 29;

U.S. Pat. No. 4,556,592 entitled "Conductive Joint Seals for Composite Aircraft" filed 1983 Dec. 12;

U.S. Pat. No. 4,475,976 entitled "Method and Apparatus for Forming Composite Material Articles" filed 1983 Dec. 23;

U.S. Pat. No. 4,469,730 entitled "Composite Base Structure and End Fitting Joint and Method" filed 1982 Dec. 30;

U.S. Pat. No. 4,370,390 entitled "3-D Chopped-Fiber Composites" filed 1981 Jun. 15;

U.S. Pat. No. 4,216,047 entitled "No-Bleed Curing of Composites" filed 1978 Sep. 15;

U.S. Pat. No. 4,086,378 entitled "Stiffened Composite Structural Member and Method of Fabrication" filed 1975 Feb. 20;

U.S. Pat. No. 3,910,105 entitled "Method for Detection of Flaws in Composite Fiberglass Structures" filed 1974 Aug. 16;

U.S. Pat. No. 8,205,833 entitled "Composite Leg Structure for a Lightweight Aircraft Seat Assembly" filed 2006 Dec. 22;

U.S. Pat. No. 8,161,619 entitled "Joint for Hybrid Composite Items" filed 2007 Nov. 2;

U.S. Pat. No. 8,044,354 entitled "Method for Classifying Resins Types in Carbon Fiber Reinforced Plastic Materials Using IR Spectroscopy" filed 2008 Dec. 4;

U.S. Pat. No. 7,968,170 entitled "Composite Single Pane Window for an Aircraft and Method of Making Same" filed 2005 Dec. 22;

U.S. Pat. No. 7,956,327 entitled "Method for Determining Degree of Aging of a Polymer Resin Material" filed 2008 Sep. 22;

U.S. Pat. No. 7,605,593 entitled "Method and Apparatus for Detecting Inconsistencies in Cured Resin Structures" filed 2007 Jan. 16;

U.S. Pat. No. 7,398,586 entitled "Methods and Systems for Manufacturing a Family of Aircraft Wings and Other Composite Structures" filed 2005 Nov. 1;

U.S. Pat. No. 6,861,017 entitled "Method for Forming Composite Parts from Volatile-Emitting Materials Using Breathable Tooling" filed 1996 Nov. 25;

U.S. Pat. No. 6,761,783 entitled "Process Method to Repair Bismaleimide (BMI) Composite Structures" filed 2002 Apr. 9;

U.S. Pat. No. 6,569,954 entitled "Composites from Blends of Advanced Oligomers" filed 1995 Jun. 7;

U.S. Pat. No. 6,436,507 entitled "Composites Joined with Z-Pin Reinforcement" filed 1999 Apr. 29;

U.S. Pat. No. 6,024,555 entitled "Tooling Having Compliant Forming Surface for Forming Resin Composites" filed 1997 Oct. 23;

U.S. Pat. No. 5,968,639 entitled "Z-Pin Reinforced, Bonded Composite Structure" filed 1997 Mar. 7;

U.S. Pat. No. 5,919,543 entitled "Composite Sine Wave Spar" filed 1997 Aug. 15;

U.S. Pat. No. 5,895,699 entitled "Tiedown Ply for Reducing Core Crush in Composite Honeycomb Sandwich Structure" filed 1996 Mar. 15;

U.S. Pat. No. 5,869,165 entitled "Highly Ordered Z-Pin Structures" filed 1997 Nov. 10;

U.S. Pat. No. 5,849,234 entitled "Multilayer Radome Structure and its Fabrication" filed 1997 Jul. 15;

U.S. Pat. No. 5,759,699 entitled "Process for Production of Low Dielectric Ceramic Composites" filed 1996 Jun. 25;

U.S. Pat. No. 5,717,191 entitled "Structural Susceptor for Thermoplastic Welding" filed 1995 Jun. 6;

U.S. Pat. No. 5,707,723 entitled "Multilayer Radome Structure and its Fabrication" filed 1996 Feb. 16;

U.S. Pat. No. 5,654,396 entitled "Polyimide Oligomers" filed 1995 Jun. 5;

U.S. Pat. No. 5,484,277 entitled "Mandreless Molding System" filed 1989 Dec. 26; U.S. Pat. No. 5,446,120 entitled "Polyethersulfone Oligomers and Blends" filed 1990 Jan. 3;

U.S. Pat. No. 5,410,133 entitled "Metal Matrix Composite" filed 1993 Jul. 15;

U.S. Pat. No. 5,376,598 entitled "Fiber Reinforced Ceramic Matrix Laminate" filed 1988 Jun. 27;

U.S. Pat. No. 5,216,117 entitled "Amideimide Blends" filed 1992 Jan. 13;

U.S. Pat. No. 5,122,176 entitled "A Method of Densifying a Glass or Glass Composite Structure" filed 1990 Jan. 17;

U.S. Pat. No. 5,112,939 entitled "Oligomers Having Pyrimidinyl End Caps" filed 1990 Jul. 10;

U.S. Pat. No. 5,104,967 entitled "Amideimide Oligomers and Blends" filed 1988 Apr. 13;

U.S. Pat. No. 5,071,941 entitled "Multidimensional Ether Sulfone Oligomers" filed 1989 Mar. 6;

U.S. Pat. No. 5,071,319 entitled "Low Maintenance, Advanced Technology Swashplate" filed 1987 Sep. 30;

U.S. Pat. No. 5,051,226 entitled "Method of Curing Composite Parts" filed 1989 Sep. 18;

U.S. Pat. No. 4,767,656 entitled "Composite Material Structure with Integral Fire Protection" filed 1984 Jan. 9;

U.S. Pat. No. 4,749,155 entitled "Method of Making Wing Box Cover Panel" filed 1985 Sep. 30;

U.S. Pat. No. 4,622,091 entitled "Resin Film Infusion Process and Apparatus" filed 1984 Nov. 29;

U.S. Pat. No. 4,556,439 entitled "Method of Sealing and Bonding Laminated Epoxy Plates" filed 1983 Dec. 12;

U.S. Pat. No. 4,318,954 entitled "Printed Wiring Board Substrates for Ceramic Chip Carriers" filed 1981 Feb. 9;

U.S. Pat. No. 4,278,485 entitled "Method of Forming Composite Wound Structure" filed 1980 May 14;

U.S. Pat. No. 4,247,255 entitled "Composite Rotor Blade Root End" filed 1979 Mar. 15;

U.S. Pat. No. 4,223,053 entitled "Truss Core Panels" filed 1978 Aug. 7;

U.S. Pat. No. 4,215,161 entitled "Fiber-Resin-Carbon Composites and Method of Fabrication" filed 1978 Mar. 20;

U.S. Pat. No. 4,136,846 entitled "Composite Structure" filed 1976 Dec. 20;

U.S. Pat. No. 8,465,241 entitled "Composite Fasteners Containing Multiple Reinforcing Fiber Types" filed 2007 Oct. 31;

U.S. Pat. No. 8,449,709 entitled "Method of Fabricating Fiber Reinforced Composite Structure Having Stepped Surface" filed 2007 May 25;

U.S. Pat. No. 8,444,087 entitled "Composite Skin and Stringer Structure and Method for Forming the Same" filed 2005 Apr. 28;

U.S. Pat. No. 8,431,214 entitled "Composite Structure Having Reinforced Core and Method of Making Same" filed 2010 Feb. 15;

U.S. Pat. No. 8,425,708 entitled "Continuous Fabrication of Parts Using In-Feed Spools of Fiber Reinforced Thermoplastic" filed 2007 Apr. 6;

U.S. Pat. No. 8,419,887 entitled "Composite Structural Member and Method for Producing the Same" filed 2012 Apr. 16;

U.S. Pat. No. 8,418,962 entitled "Distribution of Point Loads in Honeycomb Panel" filed 2008 Jan. 19;

U.S. Pat. No. 8,376,275 entitled "Energy Absorbing Structure for Aircraft" filed 2006 Dec. 8;

U.S. Pat. No. 8,349,105 entitled "Curved Composite Frames and Method of Making the Same" filed 2010 May 10;

U.S. Pat. No. 8,292,227 entitled "Aircraft Wings Having Continuously Tailored Structural Strength" filed 2008 Jul. 12;

U.S. Pat. No. 8,226,336 entitled "Systems and Methods for Material Interface Detection during Drilling Operations" filed 2007 Nov. 19;

U.S. Pat. No. 8,218,142 entitled "Fiber Optic Probe Scatterometer for Spectroscopy Measurements" filed 2009 Feb. 17;

U.S. Pat. No. 8,157,469 entitled "Composite Structural Member and Method for Producing the Same" filed 2006 Nov. 22;

U.S. Pat. No. 8,084,114 entitled "Reinforced Rampdown for Composite Structural Member and Method for Same" filed 2007 Dec. 27;

U.S. Pat. No. 7,963,126 entitled "Glass Fibers Having Improved Durability" filed 2008 Mar. 5;
U.S. Pat. No. 7,896,287 entitled "Split Torque Geared Power Transmissions with Composite Output Shafts" filed 2007 Aug. 8;
U.S. Pat. No. 7,874,518 entitled "Aircraft Structure Including Composite Beam and Composite Panel with Metal Foil There Between" filed 2006 Mar. 16;
U.S. Pat. No. 7,861,411 entitled "Composite Gear and Method of Forming Same" filed 2007 May 2;
U.S. Pat. No. 7,825,211 entitled "Single-Step-Processable Polyimides" filed 2007 Jun. 22;
U.S. Pat. No. 7,807,005 entitled "Fabrication Process for Thermoplastic Composite Parts" filed 2006 Feb. 2;
U.S. Pat. No. 7,790,277 entitled "Varied Glass Density Reinforcement of Composites" filed 2008 Sep. 20;
U.S. Pat. No. 7,716,797 entitled "Composite Seat Pan Structure for a Lightweight Aircraft Seat Assembly" filed 2006 Dec. 22;
U.S. Pat. No. 7,655,168 entitled "Tools for Manufacturing Composite Parts and Methods for Using Such Tools" filed 2006 Jan. 31;
U.S. Pat. No. 7,599,164 entitled "Lightning Protection System for Aircraft Composite Structure" filed 2006 Dec. 7;
U.S. Pat. No. 7,531,058 entitled "Reinforced Rampdown for Composite Structural Member and Method for Same" filed 2005 Feb. 24;
U.S. Pat. No. 7,527,759 entitled "Method and Apparatus for Forming Structural Members" filed 2005 Apr. 13;
U.S. Pat. No. 7,281,688 entitled "Materials for Self-Transpiring Hot Skins for Hypersonic Vehicles or Reusable Space Vehicles" filed 2006 Apr. 27;
U.S. Pat. No. 6,918,839 entitled "Damage Tolerant Shaft" filed 2002 Jan. 28;
U.S. Pat. No. 6,709,538 entitled "Method of Making a Laminated Composite Radius Filler" filed 2002 May 21;
U.S. Pat. No. 6,689,448 entitled "Method of Using a Laminated Composite Radius Filler" filed 2002 May 21;
U.S. Pat. No. 6,613,169 entitled "Thermoplastic Rewelding Process" filed 1998 Apr. 28;
U.S. Pat. No. 6,562,436 entitled "Laminated Composite Radius Filler" filed 2001 Feb. 23;
U.S. Pat. No. 6,440,521 entitled "Method for Transferring Heat in an Aircraft Engine Thrust Reverser" filed 2000 Oct. 31;
U.S. Pat. No. 6,432,507 entitled "Lightning Protection for Electrically Conductive or Insulating Skin and Core for Honeycomb Structure" filed 2000 May 18;
U.S. Pat. No. 6,284,089 entitled "Thermoplastic Seam Welds" filed 1998 Jul. 21;
U.S. Pat. No. 6,270,603 entitled "Repair Method for Uniformly Heating Composite Structure" filed 1995 Jun. 6;
U.S. Pat. No. 6,086,975 entitled "Lighting Protection for Electrically Conductive or Insulating Skin and Core for Honeycomb Structure" filed 1997 Sep. 8;
U.S. Pat. No. 6,051,089 entitled "Reinforcing Member for Composite Work Pieces and Associated Methods" filed 1998 Feb. 6;
U.S. Pat. No. 5,969,079 entitled "Oligomers with Multiple Chemically Functional End Caps" filed 1994 Oct. 21;
U.S. Pat. No. 5,958,550 entitled "Z-Pin-Reinforced Sandwich Structure" filed 1997 Mar. 5;
U.S. Pat. No. 5,910,348 entitled "Separator Film" filed 1996 Dec. 6;
U.S. Pat. No. 5,876,652 entitled "Method for Improving Pulloff Strength in Pin-Reinforced Sandwich Structure" filed 1997 Jun. 13;
U.S. Pat. No. 5,863,635 entitled "Composite Detail Having Z-Pin Stubble" filed 1997 Mar. 7;
U.S. Pat. No. 5,862,975 entitled "Composite/Metal Structural Joint with Welded Z-Pins" filed 1996 Mar. 20;
U.S. Pat. No. 5,837,318 entitled "Process for Production of Low Dielectric Ceramic Composites" filed 1995 Apr. 26;
U.S. Pat. No. 5,833,795 entitled "Magnetic Particle Integrated Adhesive and Associated Method of Repairing a Composite Material Product" filed 1996 Sep. 19;
U.S. Pat. No. 5,780,583 entitled "Reactive Polyarylene Sulfide Oligomers" filed 1991 Jan. 9;
U.S. Pat. No. 5,760,379 entitled "Monitoring the Bond Line Temperature in Thermoplastic Welds" filed 1995 Oct. 26;
U.S. Pat. No. 5,756,973 entitled "Barbed Susceptor for Improving Pulloff Strength in Welded Thermoplastic Composite Structures" filed 1995 Jun. 7;
U.S. Pat. No. 5,710,412 entitled "Fluid Tooling for Thermoplastic Welding" filed 1995 Jan. 3; U.S. Pat. No. 5,693,741 entitled "Liquid Molding Compounds" filed 1988 Mar. 15;
U.S. Pat. No. 5,688,426 entitled "Hybrid Metal Webbed Composite Beam" filed 1995 Jun. 7;
U.S. Pat. No. 5,530,089 entitled "Polysulfoneimides" filed 1988 Sep. 6;
U.S. Pat. No. 5,521,014 entitled "Extended Multidimensional Ether or Ester Oligomers" filed 1995 Jun. 5;
U.S. Pat. No. 5,447,680 entitled "Fiber-Reinforced, Titanium Based Composites and Method of Forming without Depletion Zones" filed 1994 Mar. 21;
U.S. Pat. No. 5,284,996 entitled "Waste Gas Storage" filed 1992 Feb. 28;
U.S. Pat. No. 5,268,519 entitled "Lightly Crosslinked Etherimide Oligomers" filed 1990 Sep. 25;
U.S. Pat. No. 5,239,822 entitled "Composite Structure for Thrust Reverser Torque Box" filed 1992 Jan. 14;
U.S. Pat. No. 5,175,234 entitled "Lightly Crosslinked Polyimides" filed 1989 Nov. 7;
U.S. Pat. No. 5,175,233 entitled "Multidimensional Ester or Ether Oligomers with Pyrimidinyl End Caps" filed 1992 Apr. 14;
U.S. Pat. No. 5,042,967 entitled "Drive Shaft and Rotor Hub for Helicopter Flexible Rotor System" filed 1989 Aug. 24;
U.S. Pat. No. 5,023,987 entitled "Strato Streak Flush Patch" filed 1990 May 30;
U.S. Pat. No. 5,011,905 entitled "Polyimide Oligomers and Blends" filed 1990 Aug. 13;
U.S. Pat. No. 4,898,754 entitled "Poly(amide-imide) Prepreg and Composite Processing" filed 1988 May 5;
U.S. Pat. No. 4,847,333 entitled "Blended Polyamide Oligomers" filed 1987 May 18;
U.S. Pat. No. 4,460,531 entitled "Composite Fiber Reinforced Propeller" filed 1982 May 10;
U.S. Pat. No. 4,155,970 entitled "Method for Making a Hollow Composite Using a Destructible Core" filed 1977 Nov. 4;
U.S. Pat. No. 3,978,256 entitled "Three-Dimensional Monocoque Open-Ended Annular Structure" filed 1974 Jun. 14;
U.S. Pat. No. 3,939,024 entitled "Structural Reinforced Thermoplastic Laminates and Method for Using Such Laminates" filed 1974 Apr. 10;
U.S. Pat. No. 3,936,277 entitled "Aluminum Alloy-Boron Fiber Composite" filed 1970 Apr. 9;
U.S. Pat. No. 3,755,713 entitled "Electrically Conductive Surface for Aircraft" filed 1972 Jul. 25;
U.S. Pat. No. 8,490,348 entitled "Varied Glass Density Reinforcement of Composites" filed 2010 Aug. 6;

U.S. Pat. No. 8,409,384 entitled "Predictable Bonded Rework of Composite Structures" filed 2009 Mar. 9;

U.S. Pat. No. 8,393,068 entitled "Method and Apparatus for Assembling Composite Structures" filed 2007 Nov. 6;

U.S. Pat. No. 8,338,787 entitled "System and Method for Resin Thickness Measurement" filed 2011 Jun. 1;

U.S. Pat. No. 8,337,654 entitled "Configurable Tooling and Molding Method Using the Same" filed 2007 May 11;

U.S. Pat. No. 8,298,656 entitled "Polymer Composite Structure Reinforced with Shape Memory Alloy and Method of Manufacturing Same" filed 2008 May 14;

U.S. Pat. No. 8,286,919 entitled "Impact Resistant Composite Structures" filed 2009 Jan. 8;

U.S. Pat. No. 8,228,248 entitled "Dorsal High Frequency Antenna" filed 2010 Jan. 25;

U.S. Pat. No. 8,158,210 entitled "Systems and Methods for Tape Flaw and Splice Avoidance in Manufacturing" filed 2005 Oct. 28;

U.S. Pat. No. 8,157,212 entitled "Composite Barrel Sections for Aircraft Fuselages and Other Structures, and Methods and Systems for Manufacturing Such Barrel Sections" filed 2008 Sep. 23;

U.S. Pat. No. 8,142,181 entitled "Forming Method for Composites" filed 2004 Sep. 16;

U.S. Pat. No. 8,082,667 entitled "Apparatus and Methods for Securing a First Structural Member and a Second Structural Member to One Another" filed 2007 May 31;

U.S. Pat. No. 7,963,125 entitled "Glass Fibers Having Improved Strength" filed 2008 Mar. 5;

U.S. Pat. No. 7,954,762 entitled "Lightweight Aircraft Passenger Seat with Composite Construction" filed 2006 May 17;

U.S. Pat. No. 7,841,421 entitled "Ballistic Fire Protection System" filed 2007 Jun. 7;

U.S. Pat. No. 7,837,148 entitled "Composite Wing-Body Joint" filed 2006 Jun. 13;

U.S. Pat. No. 7,770,457 entitled "Pseudo Porosity Reference Standard for Metallic Interleaved Composite Laminates" filed 2006 Oct. 13;

U.S. Pat. No. 7,730,784 entitled "Ultrasonic Method to Verify the Interference Fit of Fasteners" filed 2007 Aug. 3;

U.S. Pat. No. 7,622,066 entitled "Methods and Systems for Manufacturing Composite Parts with Female Tools" filed 2004 Jul. 26;

U.S. Pat. No. 7,431,981 entitled "Polymer Composite Structure Reinforced with Shape Memory Alloy and Method of Manufacturing Same" filed 2004 Nov. 17;

U.S. Pat. No. 7,334,782 entitled "Controlled Atmospheric Pressure Resin Infusion Process" filed 2003 May 28;

U.S. Pat. No. 7,303,700 entitled "Methods of Making Optically Clear Structural Laminates" filed 2004 Aug. 31;

U.S. Pat. No. 7,182,291 entitled "Integrated Aircraft Structural Floor" filed 2005 Mar. 23;

U.S. Pat. No. 6,827,896 entitled "Vibration Assisted Processing of Viscous Thermoplastics" filed 2003 May 9;

U.S. Pat. No. 6,797,376 entitled "Fiber-Metal Laminate Adhesive Coating" filed 2002 May 9;

U.S. Pat. No. 6,767,606 entitled "Vented Cell Structure and Fabrication Method" filed 2002 Aug. 29;

U.S. Pat. No. 6,592,799 entitled "Vibration Assisted Processing of Viscous Thermoplastics" filed 1996 Dec. 9;

U.S. Pat. No. 6,506,499 entitled "Silicon-Yttrium Sol Coating of Metals" filed 1999 Sep. 8;

U.S. Pat. No. 6,180,206 entitled "Composite Honeycomb Sandwich Panel for Fixed Leading Edges" filed 1998 Sep. 14;

U.S. Pat. No. 6,129,311 entitled "Engine Nacelle Outer Cowl Panel with Integral Track Fairings" filed 1998 Jan. 27;

U.S. Pat. No. 6,036,802 entitled "Thermoplastic Panel Bending" filed 1996 Sep. 13;

U.S. Pat. No. 5,958,578 entitled "Hybrid Laminate Having Improved Metal-to-Resin Adhesion" filed 1996 Nov. 4;

U.S. Pat. No. 5,935,475 entitled "Susceptor Integration Into Reinforced Thermoplastic Composites" filed 1998 Apr. 3;

U.S. Pat. No. 5,882,756 entitled "Composite Patches Having Z-Pin Reinforcement" filed 1997 Feb. 26;

U.S. Pat. No. 5,882,462 entitled "Method for Fabricating a Corrugated Composite Channel" filed 1996 Jun. 25;

U.S. Pat. No. 5,876,540 entitled "Joining Composites Using Z-Pinned Precured Strips" filed 1996 May 31;

U.S. Pat. No. 5,848,767 entitled "One Piece Spacecraft Frame" filed 1996 Aug. 5;

U.S. Pat. No. 5,847,375 entitled "Fastenerless Bonder Wingbox" filed 1996 Jul. 19;

U.S. Pat. No. 5,820,344 entitled "Contoured Flexure Strap for Helicopter Rotor System" filed 1997 Jun. 27;

U.S. Pat. No. 5,807,593 entitled "Vacuum Bag Not Requiring Disposable Breathers" filed 1996 Jul. 10;

U.S. Pat. No. 5,797,239 entitled "Titanium Reinforced Structural Panel Having a Predetermined Shape" filed 1997 Jan. 13;

U.S. Pat. No. 5,793,024 entitled "Bonding Using Induction Heating" filed 1995 Jun. 6;

U.S. Pat. No. 5,707,576 entitled "Process for the Fabrication of Composite Hollow Crown-Stiffened Skins and Panels" filed 1995 Jun. 7;

U.S. Pat. No. 5,594,089 entitled "Heterocycle or Heterocycle Sulfone Oligomers with Multiple Chemically Functional End Caps" file 1994 Oct. 21;

U.S. Pat. No. 5,591,369 entitled "Method and Apparatus for Consolidating Organic Matrix Composites Using Induction Heating" filed 1995 Jun. 5;

U.S. Pat. No. 5,556,565 entitled "Method for Composite Welding Using a Hybrid Metal Webbed Composite Beam" filed 1995 Jun. 7;

U.S. Pat. No. 5,530,228 entitled "Process for Consolidation of Composite Materials" filed 1995 Mar. 13;

U.S. Pat. No. 5,506,060 entitled "Method for Making Multidimensional Ether or Ester Oligomers" filed 1995 Jun. 5;

U.S. Pat. No. 5,403,666 entitled "Composites Containing Amideimide Sized Fibers" filed 1993 Jun. 21;

U.S. Pat. No. 5,344,894 entitled "Polyimide Oligomers and Blends" filed 1992 Nov. 23;

U.S. Pat. No. 5,227,216 entitled "Fiber/Metal Laminate" filed 1991 Mar. 25;

U.S. Pat. No. 5,198,526 entitled "Heterocycle Oligomers with Multidimensional Morphology" filed 1992 Jun. 26;

U.S. Pat. No. 5,159,055 entitled "Coreactive Oligomer Blends" filed 1992 Mar. 3;

U.S. Pat. No. 5,126,410 entitled "Heterocycle Oligomers" filed 1991 Sep. 18;

U.S. Pat. No. 5,120,819 entitled "High Performance Heterocycles" filed 1990 Jun. 26;

U.S. Pat. No. 5,082,905 entitled "Blended Heterocycles" filed 1991 May 6;

U.S. Pat. No. 5,069,318 entitled "Self-Stabilized Stepped Crashworthy Stiffeners" filed 1991 Jan. 7;

U.S. Pat. No. 5,031,995 entitled "Composite Reinforced Fiber for High G Loads" filed 1989 Dec. 21;

U.S. Pat. No. 5,013,507 entitled "Method for Producing an Elongate Passage Within a Component" filed 1989 Sep. 29;

U.S. Pat. No. 4,965,336 entitled "High Performance Heterocycle Oligomers and Blends" filed 1987 Nov. 3;

U.S. Pat. No. 4,917,747 entitled "Method of Making Crushed Core Molded Panels" filed 1989 Feb. 24;

U.S. Pat. No. 4,895,426 entitled "Electrically Conducting Reinforced Optical Fiber" filed 1988 Sep. 20;

U.S. Pat. No. 4,884,772 entitled "Cantilevered Vortex Control Device" filed 1986 Jul. 28;

U.S. Pat. No. 4,877,375 entitled "Drive Shaft and Rotor Hub for Helicopter Flexible Rotor System" filed 1986 Sep. 30;

U.S. Pat. No. 4,868,270 entitled "Heterocycle Sulfone Oligomers and Blends" filed 1987 Nov. 17;

U.S. Pat. No. 4,859,267 entitled "Method for Consolidating Composite Materials" filed 1987 Sep. 28;

U.S. Pat. No. 4,797,155 entitled "Method for Making Metal Matrix Composites" filed 1987 Feb. 27;

U.S. Pat. No. 4,765,942 entitled "Method of Consolidating Thermoplastic Poly(Amide-Imide) Components" filed 1986 Sep. 30;

U.S. Pat. No. 4,765,602 entitled "Composite Coil Spring" filed 1982 Dec. 22;

U.S. Pat. No. 4,726,924 entitled "Method of Planar Forming of Zero Degree Composite Tape" filed 1986 Apr. 14;

U.S. Pat. No. 4,715,923 entitled "Apparatus for Consolidating Composite Materials" filed 1985 Dec. 26;

U.S. Pat. No. 4,696,711 entitled "Method for Forming Holes in Composites" filed 1983 Sep. 30;

U.S. Pat. No. 4,606,961 entitled "Discretely Stiffened Composite Panel" filed 1984 Oct. 9;

U.S. Pat. No. 4,579,699 entitled "Method for Making A-Si3 N4 Whiskers and Articles Therefrom" filed 1983 Sep. 29;

U.S. Pat. No. 4,301,707 entitled "Embedded Explosive Severance of Non-Metallic Materials" filed 1979 Oct. 29;

U.S. Pat. No. 4,100,322 entitled "Fiber-Resin-Carbon Composites and Method of Fabrication" filed 1974 Dec. 11;

U.S. Pat. No. 4,038,118 entitled "Three Dimensional Composite Structure and Method for Incorporating Fittings" filed 1976 Mar. 4;

U.S. Pat. No. 3,951,718 entitled "Method for Producing Reinforced Insulating Foam" filed 1975 Jan. 3;

U.S. Pat. No. 3,881,972 entitled "Continuous Process and Machine" filed 1973 Oct. 2;

U.S. Pat. No. 3,814,275 entitled "Cryogenic Storage Vessel" filed 1972 Apr. 3;

U.S. Pat. No. 8,006,722 entitled "Pipeline for Conducting Air for Air Conditioning in Aircrafts" filed 2006 May 15;

U.S. Pat. No. 7,896,294 entitled "Cover Skin for a Variable-Shape Aerodynamic Area" filed 2005 Nov. 23;

U.S. Pat. No. 8,215,885 entitled "Lockable Fastener Assembly" filed 2007 Sep. 20;

U.S. Pat. No. 7,895,810 entitled "Crash Paddle for Reinforcing a Primary Fuselage Structure of an Aircraft" filed 2008 Jan. 18;

U.S. Pat. No. 7,766,281 entitled "System for Reducing Aerodynamic Noise at a Supplementary Wing of an Aircraft" filed 2005 Nov. 9;

US20130156979A1 entitled "Composite Columnar Structure Having Co-Bonded Reinforcement and Fabrication Method" which was published 2013 Jun. 20;

US20130153145A1 entitled "Systems and Methods for Reducing Noise in Aircraft Fuselages and Other Structures" which was published 2013 Jun. 20;

US20130122236A1 entitled "Composite Structures Having Composite-To-Metal Joints and Method for Making the Same" which was published 2013 May 16;

US20130105072A1 entitled "Method and Apparatus for Producing Composite Fillers" which was published 2013 May 2;

US20130087380A1 entitled "Thin Wall Bushing for Robust Electrical Bonding to Fiber-Reinforced Structures" which was published 2013 Apr. 11;

US20130084434A1 entitled "Curved Composite Frames and Method of Making the Same" which was published 2013 Apr. 4;

US20130075526A1 entitled "Multi-Layer Metallic Structure and Composite-to-Metal Joint Methods" which was published 2013 Mar. 28;

US20130047403A1 entitled "Compression Molding Method and Reinforced Thermoplastic Parts Molded Thereby" which was published 2013 Feb. 28;

US20130036922A1 entitled "Method and Device for Transporting, Placing and Compacting Composite Stiffeners" which was published 2013 Feb. 14;

US20130034705A1 entitled "Molybdenum Composite Hybrid Laminates and Methods" which was published 2013 Feb. 7;

US20130022391A1 entitled "Molded-In Insert and Method for Fiber Reinforced Thermoplastic Composite Structure" which was published 2013 Jan. 24;

US20130014889A1 entitled "Rapid Fabrication of a Composite Part" which was published 2013 Jan. 17;

US20130014378A1 entitled "Cell Including Clean and Dirty Sections for Fabricating Composite Parts" which was published 2013 Jan. 17;

US20130014372A1 entitled "Rotary Mandrel Tool Support" which was published 2013 Jan. 17;

US20120288664A1 entitled "Methods and Preforms for Forming Composite Members with Interlayers Formed of Nonwoven, Continuous Materials" which was published 2012 Nov. 15;

US20120234972A1 entitled "Composite Leg for Landing Gear Assembly" which was published 2012 Sep. 20;

US20120223187A1 entitled "Diamond Shaped Window for Composite and/or Metallic Airframe" which was published 2012 Sep. 6;

US20120199271A1 entitled "Composite Structural Member and Method for Producing the Same" which was published 2012 Aug. 9;

US20120197482A1 entitled "Embedded Damage Detection System for Composite Materials of an Aircraft" which was published 2012 Aug. 2;

US20120193016A1 entitled "Sandwich Structure Having Arrestment Feature and Method of Making the Same" which was published 2012 Aug. 2;

US20120183347A1 entitled "Joint for Composite Tube" which was published 2012 Jul. 19;

US20120168071A1 entitled "Method and Device for Compressing a Composite Radius" which was published 2012 Jul. 5;

US20120149802A1 entitled "Composites Having Distortional Resin Coated Fibers" which was published 2012 Jun. 14;

US20120141705A1 entitled "Wrinkle Control for Composite Tubes" which was published 2012 Jun. 7;

US20120121866A1 entitled "Method of Laying Up Prepreg Plies on Contoured Tools Using a Deformable Carrier Film" which was published 2012 May 17;

US20120097321A1 entitled "Systems and Methods for Reducing Noise in Aircraft Fuselages and Other Structures" which was published 2012 Apr. 26;

US20120076989A1 entitled "Method and Apparatus for Fabricating Highly Contoured Composite Stiffeners with Reduced Wrinkling" which was published 2012 Mar. 29;

US20120067514A1 entitled "Method and Apparatus for Making Fiber Reinforced Composite Tubes" which was published 2012 Mar. 22;

US20120067513A1 entitled "Composite Leg Structure for a Lightweight Aircraft Seat Assembly" which was published 2012 Mar. 22;

US20120052305A1 entitled "Composite Structures Using Interpenetrating Polymer Network Adhesives" which was published 2012 Mar. 1;

US20120052247A1 entitled "Composite Structures Having Integrated Stiffeners with Smooth Runouts and Method of Making the Same" which was published 2012 Mar. 1;

US20120045606A1 entitled "Composite Structures Having Composite-to-Metal Joints and Method for Making the Same" which was published 2012 Feb. 23;

US20110315824A1 entitled "Composite Structures Having Integrated Stiffeners and Method of Making the Same" which was published 2011 Dec. 29;

US20110311778A1 entitled "Bead-Stiffened Composite Parts" which was published 2011 Dec. 22;

US20110300358A1 entitled "Shape Memory Alloy/Fiber Reinforced Polymeric Composite Structures and Method for Forming" which was published 2011 Dec. 8;

US20110281114A1 entitled "Method of Making a Composite Sandwich Structure and Sandwich Structure Made Thereby" which was published 2011 Nov. 17;

US20110252742A1 entitled "Composite Structures Having Reinforced Edge Bonded Joints and Method for Making the Same" which was published 2011 Oct. 20;

US20110230597A1 entitled "Glass Fibers Having Improved Durability" which was published 2011 Sep. 22;

US20110230596A1 entitled "Glass Fibers Having Improved Strength" which was published 2011 Sep. 22;

US20110195230A1 entitled "Apparatuses, Systems, and Methods for Manufacturing Composite Parts" which was published 2011 Aug. 11;

US20110135887A1 entitled "Sandwich Structure Having Arrestment Feature and Method of Making the Same" which was published 2011 Jun. 9;

US20110111172A1 entitled "Compression Molding Method and Reinforced Thermoplastic Parts Molded Thereby" which was published 2011 May 12;

US20110097554A1 entitled "Curved Composite Frames and Method of Making the Same" which was published 2011 Apr. 28;

US20110045232A1 entitled "Composite Stiffeners for Aerospace Vehicles" which was published 2011 Feb. 24;

US20110006460A1 entitled "Curing System and Method Using Electromagnetic Force and Conductive Heat Transfer" which was published 2011 Jan. 13;

US20100320320A1 entitled "Aerospace Structure Including Composite Beam Chord Clamped Between Reinforcement Plates" which was published 2010 Dec. 23;

US20100320319A1 entitled "Systems and Methods for Reducing Noise in Aircraft Fuselages and Other Structures" which was published 2010 Dec. 23;

US20100319841A1 entitled "Novel Fabrication Process for Thermoplastic Composite Parts" which was published 2010 Dec. 23;

US20100316859A1 entitled "Varied Glass Density Reinforcement of Composites" which was published 2010 Dec. 16;

US20100282904A1 entitled "Aircraft Having a Forward-Facing Section that Deflects Elastically Under Impact Loads" which was published 2010 Nov. 11;

US20100276578A1 entitled "Method for Determining Degree of Aging of a Polymer Resin Material" which was published 2010 Nov. 4;

US20100264266A1 entitled "Metal-Coated Fabrics for Fiber-Metal Laminates" which was published 2010 Oct. 21;

US20100247838A1 entitled "Method of Making Bead-Stiffened Composite Parts and Parts Made Thereby" which was published 2010 Sep. 30;

US20100233424A1 entitled "Composite Structures Employing Quasi-Isotropic Laminates" which was published 2010 Sep. 16;

US20100227117A1 entitled "Tapered Patch for Predictable Bonded Rework of Composite Structures" which was published 2010 Sep. 9;

US20100227106A1 entitled "Predictable Bonded Rework of Composite Structures Using Tailored Patches" which was published 2010 Sep. 9;

US20100219294A1 entitled "Composite Beam Chord Between Reinforcement Plates" which was published 2010 Sep. 2;

US20100208238A1 entitled "Fiber Optic Probe Scatterometer for Spectroscopy Measurements" which was published 2010 Aug. 19;

US20100187894A1 entitled "Composite Seat Pan Structure for a Lightweight Aircraft Seat Assembly" which was published 2010 Jul. 29;

US20100151189A1 entitled "Composite Structure Having Reinforced Core and Method of Making Same" which was published 2010 Jun. 17;

US20100140476A1 entitled "Method for Classifying Resins Types in Carbon Fiber Reinforced Plastic Materials Using IR Spectroscopy" which was published 2010 Jun. 10;

US20100133039A1 entitled "Hybrid Composite Structure Having Damped Metallic Fibers and Method for Making the Same" which was published 2010 Jun. 3;

US20100121475A1 entitled "Method of Manufacturing Co-Molded Inserts" which was published 2010 May 13;

US20100078845A1 entitled "Wrinkle Reduction in Uncured Composite Laminates" which was published 2010 Apr. 1;

US20100075090A1 entitled "Varied Glass Density Reinforcement of Composites" which was published 2010 Mar. 25;

US20100068326A1 entitled "Tools for Manufacturing Composite Parts and Methods for Using Such Tools" which was published 2010 Mar. 18;

US20100011702A1 entitled "Opaque Fiber Reinforcement of Composites" which was published 2010 Jan. 21;

US20100006700A1 entitled "Aircraft Wings Having Continuously Tailored Structural Strength" which was published 2010 Jan. 14;

US20090317587A1 entitled "Reinforced Stiffeners and Method for Making the Same" which was published 2009 Dec. 24;

US20090277992A1 entitled "Composite Leg for Landing Gear Assembly" which was published 2009 Nov. 12;

US20090261199A1 entitled "Method for Producing Contoured Composite Structures and Structures Produced Thereby" which was published 2009 Oct. 22;

US20090226746A1 entitled "Method for Making Hybrid Metal-Ceramic Matrix Composite Structures and Structures Made Thereby" which was published 2009 Sep. 10;

US20090226709A1 entitled "Glass Fibers Having Improved Durability" which was published 2009 Sep. 10;
US20090226692A1 entitled "Glass Fibers Having Improved Strength" which was published 2009 Sep. 10;
US20090206202A1 entitled "Energy Absorbing Structure for Aircraft" which was published 2009 Aug. 20;
US20090202767A1 entitled "Wrinkle Control for Composite Tubes" which was published 2009 Aug. 13;
US20090184204A1 entitled "Distribution of Point Loads in Honeycomb Panels" which was published 2009 Jul. 23;
US20090181211A1 entitled "Distortion Resistant Transparent Reinforcing Fibers for Use in Transparent Reinforced Composites" which was published 2009 Jul. 16;
US20090148647A1 entitled "Method of Fabricating Structures Using Composite Modules and Structures Made Thereby" which was published 2009 Jun. 11;
US20090104398A1 entitled "Composite Article Having Reinforcing Fibers Oriented to Suppress or Delay Ply Splitting" which was published 2009 Apr. 23;
US20090095413A1 entitled "Composite Reinforcement of Metallic Structural Elements" which was published 2009 Apr. 16;
US20090056109A1 entitled "Methods and Systems for Manufacturing a Family of Aircraft Wings and Other Composite Structures" which was published 2009 Mar. 5;
US20090035510A1 entitled "Composite Structure Having Reinforced Core and Method of Making Same" which was published 2009 Feb. 5;
US20090005232A1 entitled "Composite Structures Having Reinforced Edge Bonded Joints and Method for Making the Same" which was published 2009 Jan. 1;
US20090004425A1 entitled "Ceramic Matrix Composite Structure Having Fluted Core and Method for Making the Same" which was published 2009 Jan. 1;
US20080302915A1 entitled "Manufacturing Process Using Bladderless Mold Line Conformal Hat Stringer" which was published 2008 Dec. 11;
US20080300360A1 entitled "Water-Entrained-Polyimide Chemical Compositions for Use in High-Performance Composite Fabrication" which was published 2008 Dec. 4;
US20080289747A1 entitled "Method of Fabricating Fiber Reinforced Composite Structure Having Stepped Surface" which was published 2008 Nov. 27;
US20080277531A1 entitled "Hybrid Composite Panel Systems and Methods" which was published 2008 Nov. 13;
US20080277057A1 entitled "Composite Laminate Having a Damping Interlayer and Method of Making the Same" which was published 2008 Nov. 13;
US20080210820A1 entitled "Aircraft Floor and Method of Assembly" which was published 2008 Sep. 4;
US20080196475A1 entitled "Porosity Reference Standard Utilizing One or More Hollow, Non-Cylindrical Shafts" which was published 2008 Aug. 21;
US20080174306A1 entitled "Method and Apparatus for Detecting Inconsistencies in Fiber Reinforced Resin Parts Using Eddy Currents" which was published 2008 Jul. 24;
US20080138584A1 entitled "Reinforced Rampdown for Composite Structural Member and Method for Same" which was published 2008 Jun. 12;
US20080131630A1 entitled "Composite Tube Having Cobonded End Fittings and Method of Making Same" which was published 2008 Jun. 5;
US20080129041A1 entitled "Composite Tube Having Co-Bonded End Fittings" which was published 2008 Jun. 5;
US20080128430A1 entitled "Edge Seals for Composite Structure Fuel Tanks" which was published 2008 Jun. 5;
US20080128078A1 entitled "Curie Temperature Controlled Induction Heating" which was published 2008 Jun. 5;
US20080121039A1 entitled "Porosity Reference Standard Utilizing One or More Discrete Wires" which was published 2008 May 29;
US20080118303A1 entitled "Composite Structural Member and Method For Producing The Same" which was published 2008 May 22;
US20080054523A1 entitled "Apparatuses, Systems, and Methods for Manufacturing Composite Parts" which was published 2008 Mar. 6;
US20070176323A1 entitled "Tools for Manufacturing Composite Parts and Methods for Using Such Tools" which was published 2007 Aug. 2;
US20070175572A1 entitled "Continuous Fabrication of Parts Using In-Feed Spools of Fiber Reinforced Thermoplastic" which was published 2007 Aug. 2;
US20070125177A1 entitled "Tapered Ultrasonic Reference Standard" which was published 2007 Jun. 7;
US20070119256A1 entitled "Porosity Reference Standard Utilizing One or More Discrete Wires" which was published 2007 May 31;
US20070107520A1 entitled "Porosity Reference Standard Utilizing a Mesh" which was published 2007 May 17;
US20070096751A1 entitled "Systems and Methods for Inspecting Electrical Conductivity in Composite Materials" which was published 2007 May 3;
US20070089479A1 entitled "Ultrasonic Inspection Reference Standard for Porous Composite Materials" which was published 2007 Apr. 26;
US20070034743A1 entitled "Composite Single Pane Window for an Aircraft and Method of Making Same" which was published 2007 Feb. 15;
US20070022707A1 entitled "Composite Structural Member Having an Undulating Web and Method for Forming Same" which was published 2007 Feb. 1;
US20070000596A1 entitled "Methods of Forming Metal Foil Ply Replacement in Composite Structures" which was published 2007 Jan. 4;
US20060283133A1 entitled "Composite Reinforcement of Metallic Structural Elements" which was published 2006 Dec. 21;
US20060243860A1 entitled "Composite Skin and Stringer Structure and Method for Forming the Same" which was published 2006 Nov. 2;
US20060237588A1 entitled "Composite Structural Member Having an Undulating Web and Method for Forming the Same" which was published 2006 Oct. 26;
US20060236652A1 entitled "Composite Structural Members and Methods for Forming the Same" which was published 2006 Oct. 26;
US20060213250A1 entitled "Ultrasonic Inspection Reference Standard for Composite" which was published 2006 Sep. 28;
US20060188696A1 entitled "Reinforced Rampdown for Composite Structural Member and Method for Same" which was published 2006 Aug. 24;
US20060062650A1 entitled "Hybrid Fastener Apparatus and Method for Fastening" which was published 2006 Mar. 23;
US20050059309A1 entitled "Methods and Preforms for Forming Composite Members with Interlayers Formed of Nonwoven, Continuous Materials" which was published 2005 Mar. 17;
US20050048260A1 entitled "Method and Apparatus for Fabricating a Laminated Fiber Metal Composite" which was published 2005 Mar. 3;

US20050035478A1 entitled "Method and Apparatus for Vacuum Assisted Resin Transfer Molding" which was published 2005 Feb. 17;

US20030196741A1 entitled "Textile Joint Reinforcement and Associated Method" which was published 2003 Oct. 23;

US20030193516A1 entitled "Method of Fabricating a Damage Tolerant Shaft" which was published 2003 Oct. 16;

US20030190455A1 entitled "Textile Joint Reinforcement and Associated Method" which was published 2003 Oct. 9;

US20030188821A1 entitled "Process Method to Repair Bismaleimide (BMI) Composite Structures" which was published 2003 Oct. 9;

US20030144062A1 entitled "Damage Tolerant Shaft and Associated Fabrication Method" which was published 2003 Jul. 31;

US20030024630A1 entitled "Method of Making a Laminated Composite Radius Filler" which was published 2003 Feb. 6;

US20020038687A1 entitled "Thermoplastic Seam Welds" which was published 2002 Apr. 4;

US20020031641A1 entitled "Laminated Composite Radius Filler" which was published 2002 Mar. 14;

US20130149498A1 entitled "Method of Fabricating Composite Laminate Structures Allowing Ply Slippage During Forming" which was published 2013 Jun. 13;

US20130129970A1 entitled "Sandwich Structure Having Arrestment Feature" which was published 2013 May 23;

US20130056672A1 entitled "Method, Apparatus and Material Mixture for Direct Digital Manufacturing of Fiber Reinforced Parts" which was published 2013 Mar. 7;

US20130020438A1 entitled "Flexible Truss Frame and Method of Making the Same" which was published 2013 Jan. 24;

US20130018499A1 entitled "Producibility Analysis During Engineering Design of Composite Parts" which was published 2013 Jan. 17;

US20130014888A1 entitled "Masterless Layup Mandrel Tool" which was published 2013 Jan. 17;

US20130014367A1 entitled "Large Area Repair of Composite Aircraft" which was published 2013 Jan. 17;

US20120213985A1 entitled "Continuous, Carbon-Nanotube-Reinforced Polymer Precursors and Carbon Fibers" which was published 2012 Aug. 23;

US20120171410A1 entitled "Contoured Composite Parts" which was published 2012 Jul. 5;

US20120152611A1 entitled "Electrically Conductive Bushing Connection to Structure for Current Path" which was published 2012 Jun. 21;

US20110262730A1 entitled "Continuous Carbon-Nanotube-Reinforced Polymer Precursors and Carbon Fibers" which was published 2011 Oct. 27;

US20100276065A1 entitled "Bonded Patches With Bond Line Control" which was published 2010 Nov. 4;

US20100227105A1 entitled "Predictable Bonded Rework of Composite Structures" which was published 2010 Sep. 9;

US20100120969A1 entitled "Continuous, Carbon-Nanotube-Reinforced Polymer Precursors and Carbon Fibers" which was published 2010 May 13;

US20100074979A1 entitled "Methods and Systems for Manufacturing Composite Parts with Female Tools" which was published 2010 Mar. 25;

US20090283635A1 entitled "Impact Resistant Composite Structures" which was published 2009 Nov. 19;

US20090263618A1 entitled "Method for Producing Contoured Composite Structures and Structures Produced Thereby" which was published 2009 Oct. 22;

US20090218713A1 entitled "Vacuum Heat-Set of Net Shape Latex Vacuum Bags" which was published 2009 Sep. 3;

US20090084899A1 entitled "Composite Wing-Body Joint" which was published 2009 Apr. 2;

US20090031811A1 entitled "Ultrasonic Method to Verify the Interference Fit of Fasteners" which was published 2009 Feb. 5;

US20090019685A1 entitled "Composite Structure Having Ceramic Truss Core and Method for Making the Same" which was published 2009 Jan. 22;

US20080319159A1 entitled "Single-Step-Processable Polyimides" which was published 2008 Dec. 25;

US20080277058A1 entitled "Configurable Tooling and Molding Method Using the Same" which was published 2008 Nov. 13;

US20080254274A1 entitled "Polymer Composite Structure Reinforced with Shape Memory Alloy and Method of Manufacturing Same" which was published 2008 Oct. 16;

US20080169828A1 entitled "Method and Apparatus for Detecting Inconsistencies in Cured Resin Structures" which was published 2008 Jul. 17;

US20060231981A1 entitled "Method and Apparatus for Forming Structural Members" which was published 2006 Oct. 19;

US20060214058A1 entitled "Integrated Aircraft Structural Floor" which was published 2006 Sep. 28;

US20060071124A1 entitled "Reinforced Structural Assembly Having a Lap Joint and Method for Forming the Same" which was published 2006 Apr. 6;

US20040126537A1 entitled "Vented Cell Structure and Fabrication Method" which was published 2004 Jul. 1.

US20130115404A1 entitled "Lightweight Structure, Particularly Primary Aircraft Structure or Subassembly, As Well As Method for the Manufacture Thereof" which was published on 2013 May 9;

US20120153083A1 entitled "Optimization of Structures Subjected to Hot Gas Streams" which was published on 2012 Jun. 21;

US20110088538A1 entitled "Method and Device for Producing Fiber-Reinforced Plastic Profile Parts" which was published on 2011 Apr. 21;

US20090260706A1 entitled "Pipeline for Conducting Air for Air Conditioning in Aircrafts" which was published on 2009 Oct. 22;

US20060163431A1 entitled "Cover Skin for a Variable-Shape Aerodynamic Area" which was published on 2006 Jul. 27;

US20130099056A1 entitled "Fuselage Cell for an Aircraft, Particularly an Airplane" which was published on 2013 Apr. 25;

US20080251647A1 entitled "System for Reducing Aerodynamic Noise at a Supplementary Wing of an Aircraft" which was published on 2008 Oct. 16.

Non-Patent Literature

Each of the following non-patent references is related to the subject matter of the present application and each below identified reference is incorporated herein in its entirety by reference.

The book entitled "The Art of Electronics" by Paul Horowitz and Winfield Hill, Second Edition, Cambridge University Press, © 1989, 22nd printing 2008.

The book entitled "Student Manual for The Art of Electronics" by Thomas C. Hayes and Paul Horowitz, Cambridge University Press, © 1989, 22nd printing 2010.

The book entitled "Physics, Parts I & 2", Third Edition, by David Halliday and Robert Resnick, John Wiley & Sons, © 1978.

The book entitled "The AARL Handbook for Radio Communications", 2012 Edition, Edited by H. Ward Silver, published by the National Association for Amateur Radio™ (AARL).

The book entitled "Electronics Designers' Handbook", Second Edition, Edited by L. G. Giacoletto, © 1977, McGraw-Hill Book Company.

The book entitled the "IC Op-Amp Cookbook", Third Edition, by Walter J. Jung, © 1986, Howard W. Sams & Company.

The book entitled "Introductory Electronics for Scientists and Engineers", by Robert E. Simpson, © 1974, Allyn and Bacon, Inc. of Boston.

The book entitled "Electronics for Scientists—Principles and Experiments for Those Who Use Instruments", by H. V. Malmstadt and C. G. Enke, © 1962, W. A. Benjamin, Inc. of New York.

The book entitled the "American Institute of Physics Handbook", Second Edition, Edited by Dwight E. Gray, Ph.D., © 1963, McGraw-Hill Book Company.

The book entitled "The Encyclopedia of Physics", Second Edition, Edited by Robert M. Basancon, © 1974, Van Nostrand Reinhold Company.

The book entitled "Van Nostrand's Scientific Encyclopedia", Fifth Edition, Edited by Douglas M. Considine, © 1976, Van Nostrand Reinhold Company.

The book entitled "Handbook of Physics", Second Edition, Edited by E. U. Condon and Hugh Odishaw, © 1967, McGraw-Hill Book Company.

The book entitled "Handbook of Physics", Second Edition, by B. Yavorsky and A. Detlaf, © 1975, translated from Russian by Nicholas Weinstein, English translation published by Mir Publishers, Moscow.

The book entitled "Physics, Physical Science Study Committee", © 1960, Library of Congress Catalog Card Number 60-13412, D.C. Heath and Company.

The book entitled "Modern Physics" by Dull, Metcalfe and Williams, © 1960, Henry Holt and Company.

The book entitled "Experiments in Modern Physics", by Adrian C. Melissinos, © 1966, Academic Press Inc.

The book entitled "Theory and Problems of Modern Physics", Gautreau and Savin, Schaum's Outline Series, © 1978, McGraw-Hill, Inc.

The book entitled "Applied Physics", Third Edition, Arthur Beiser, Schaum's Outline Series, © 1995, McGraw-Hill, Inc.

The book entitled "A Physicist's Desk Reference", "Second Edition of Physics Vade Mecum", Edited by Herbert L. Anderson, © 1989, Springer-Verlag.

The book entitled "Theoretical Physics", Third Edition, by Georg Joos, © 1964, Hafner Publishing Company, New York The book entitled "Experimental Atomic Physics" by Harnwell and Livingood, © 1933, McGraw-Hill Book Company.

The book entitled "Concepts in Electricity and Magnetism", by Reuben Benumof, © 1961, Holt, Rinehart and Winston, Inc.

The book entitled "Modern Optical Engineering, The Design of Optical Systems", by Warren J. Smith, © 1966, McGraw-Hill Book Company.

The book entitled "The Handbook of Optics", Edited by Walter G. Driscoll, Sponsored by the Optical Society of America, © 1978, McGraw-Hill, Inc.

The book entitled "Introduction to Modern Optics", by Grant R. Flowles, © 1968, Holt, Rinehart and Winston, Inc.

The book entitled "Fluid Mechanics and Hydraulics", Third Edition, Shaum's Outline Series, Giles, Evett, and Liu, © 1994, McGraw-Hill Companies Inc.

The book entitled "Fundamental of Fluid Mechanics", Fifth Edition, Munson, Young, Okiishi, © 2006, John Wiley & Sons, Inc.

The book entitled "The Acoustical Foundations of Music, Musical sound; its properties, production, behavior and reproduction", Second Edition, by John Backus, © 1977, W. W. Norton & Company, Inc.

The book entitled "Principles of the Theory of Solids", J. M. Ziman, © 1965, Cambridge at the University Press.

The book entitled "Introduction to Solid State Physics", Fifth Edition, by Charles Kittel, © 1976, John Wiley & Sons.

The book entitled "Classical Dynamics of Particles and Systems", Jerry B. Marion, © 1965, Academic Press.

The book entitled "Light-Sensitive Systems: Chemistry and Application of Nonsilver Halide Photographic Processes", by Jaromir Kosar, © 1965, John Wiley & Sons.

The book entitled "Photochromism", that is Volume III in the Series called "Techniques of Chemistry", Edited by Glenn H. Brown, © 1971, Wiley-Interscience, a Division of John Wiley & Sons, Inc.

The book entitled "Lange's Handbook of Chemistry", Twelfth Edition, Edited by John A. Dean, © 1979, McGraw-Hill Book Company.

The book entitled "Practical Instrumentation Transducers" by Frank J. Oliver, © 1971, Hayden Book Company.

The book entitled "Formulas for Natural Frequency and Mode Shape", Robert D. Blevins Ph.D., © 1984, ISBN 0-89874-791-0, Robert E. Kreiger Publishing Company.

The book entitled "Transmission Systems for Communications", Fifth Edition, © 1982, Members of the Staff, Bell Telephone Laboratories, Inc.

The book entitled "Fields and Waves in Communications Electronics", Second Edition, Ramo, Whinnery and Van Duzer, © 1984, John Wiley & Sons.

The book entitled "Antennas in Matter, Fundamental, Theory, and Applications", by King, Smith, Owens and Wu, © 1981, ISBN 0-262-11074-1, The MIT Press, Cambridge, Mass.

The book entitled "Advanced Lithium-Ion Batteries (New Materials for Sustainable Energy and Development) by Dr. Abbas Nazri.

The book entitled "Battery Management Systems for Large Lithium-Ion Battery Packs" by David Andrea.

The book entitled "Lithium-Ion Batteries: Science and Technologies" by Yoship et. al.

The book entitled "Process Instruments and Controls Handbook", Third Edition, Edited by Douglas M. Considine, © 1985, McGraw-Hill Book Company.

The book entitled "Feedback and Control Systems", Second Edition, Schaum's Outline Series, by Distefano III, Stubberud and Williams, © 1990, McGraw-Hill Book Company.

The book entitled "Strength of Materials", Fourth Edition, Schaum's Outline Series by William Nash, © 1998, McGraw-Hill Book Company.

The book entitled "Developments in Fiber-Reinforced Polymer (Frp) Composites for Civil Engineering", part of the Woodhead Publishing Series in Civil and Structural Engineering, by Nasim Uddin, ISBN 9780857092342.

The book entitled "Fiber-Reinforced Composites: Materials, Manufacturing, and Design", by P. K. Mallick, © 2007, CRC Press.

The book entitled "Stress Analysis of Fiber-reinforced Composite Materials", by Michael W. Haywer, © 2008, Destech Publications, Inc. available through Powell's Books.

And finally, the book entitled "Fatigue of Fiber-Reinforced Composites (Engineering Materials and Processes", by Anastasios P. Vassilopoulos, © 2011, Springer Publishers.

While the above description contains many specificities, these should not be construed as limitations on the scope of the invention, but rather as exemplification of preferred embodiments thereto. As have been briefly described, there are many possible variations. Accordingly, the scope of the invention should be determined not only by the embodiments illustrated, but by any appended claims and their legal equivalents that will eventually issue in a relevant patent or patents.

What is claimed is:

1. A real time electronics measurement system to assess failure of a portion of an aircraft made at least in part with fiber reinforced composite material comprising, measurement means fabricated within the wing and wing-box portion of an aircraft to detect the invasion of fluids and gases into compression induced microfractures of the fiber-reinforced composite materials, communication means for outputting data generated by the measurement means, and a remote receiver for receiving the data output.

2. The real time electronics measurement system of claim 1, wherein the remote receiver comprises at least one of a computer and hand held device.

3. The real time electronics measurement system of claim 1, wherein the communication means transmits data to the receiver by at least one of radio frequency, cellular and Wi-Fi.

4. The real time electronics measurement system of claim 1, wherein the data output from the communication means includes an alarm.

5. The real time electronics measurement system of claim 1, further comprising a communications module that is programmable to automatically initiate transmission of data to at least one remote receiver by the communication means following arrival of the aircraft at an airport.

6. A real time electronics measurement system comprising, measurement means to measure the differential resistivity of fiber reinforced composite materials fabricated within the wing and wing-box portion of an aircraft to detect the invasion of fluids and gases into compression induced microfractures of said fiber-reinforced composite materials, communication means for outputting data generated by the measurement means, and a remote receiver for receiving the data output of the communication means.

* * * * *